United States Patent
Senderoff et al.

(10) Patent No.: US 10,232,046 B2
(45) Date of Patent: *Mar. 19, 2019

(54) HEMOSTATIC MICROSPHERES

(71) Applicant: Baxter International, Inc., Deerfield, IL (US)

(72) Inventors: Richard I. Senderoff, Edmonds, WA (US); Jeffrey D. Meyer, Lake Forest Park, WA (US); Emily N. Rollins, Seattle, WA (US); Steven D. Hughes, Kenmore, WA (US); Richard M. Garcia, Kirkland, WA (US); Paul D. Bishop, Fall City, WA (US); Gerald W. Lasser, Lynnwood, WA (US)

(73) Assignee: Baxter International Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/463,698

(22) Filed: Mar. 20, 2017

(65) Prior Publication Data

US 2017/0189537 A1 Jul. 6, 2017

Related U.S. Application Data

(62) Division of application No. 12/935,114, filed as application No. PCT/US2009/038320 on Mar. 26, 2009, now Pat. No. 9,629,798.

(60) Provisional application No. 61/042,156, filed on Apr. 3, 2008, provisional application No. 61/150,466, filed on Feb. 6, 2009.

(51) Int. Cl.
| | |
|---|---|
| *A61K 47/42* | (2017.01) |
| *A61K 38/48* | (2006.01) |
| *A61K 47/38* | (2006.01) |
| *A61K 47/32* | (2006.01) |
| *A61K 9/00* | (2006.01) |
| *A61K 9/06* | (2006.01) |
| *A61K 47/10* | (2017.01) |
| *A61K 47/26* | (2006.01) |

(52) U.S. Cl.
CPC ............ *A61K 47/42* (2013.01); *A61K 9/0024* (2013.01); *A61K 9/06* (2013.01); *A61K 38/4833* (2013.01); *A61K 47/10* (2013.01); *A61K 47/26* (2013.01); *A61K 47/32* (2013.01); *A61K 47/38* (2013.01); *C12Y 304/21005* (2013.01); *Y10T 428/2982* (2015.01)

(58) Field of Classification Search
None
See application file for complete search history.

(56) References Cited

U.S. PATENT DOCUMENTS

| | | | | |
|---|---|---|---|---|
| 4,891,359 | A * | 1/1990 | Saferstein | A61L 24/0015 424/499 |
| 8,821,918 | B2 * | 9/2014 | Greff | A61L 26/0038 424/443 |
| 2005/0037088 | A1 | 2/2005 | Pendharkar et al. | |
| 2005/0284809 | A1 * | 12/2005 | Looney | A61L 24/0036 210/502.1 |
| 2006/0204490 | A1 | 9/2006 | Pendharkar et al. | |

OTHER PUBLICATIONS

Canadian Application No. 2,716,010 Office Action dated Feb. 22, 2016, 6 pages.
Lewis, K.M. et al, Comparison of two gelatin and thrombin combination hemostats in a porcine liver abrasion model, J. Invest Surg., 2013 pp. 141-8, vol. 26, No. 2.
Gelfoam absorbable gelatin powder product sheet; Pharma and Upjohn Company; revised Jun. 2013 (10 pages).
Canter et al., "Gelfoam and Thrombin in Treatment of Massive Gastroduodenal Hemorrhage", A Preliminary Report; American Journal of Surgery, Dec. 1950, pp. 883-887.
Surgiflo Hemostatic Matrix Kit with Thrombin, Instructions for Use; Ethicon, Inc., 2011 (16 pages).
Sonomura, Tetsuo et al., "Uterine damage in swine following uterine artery embolization: comparison among gelatin sponge particles and two concentrations of N-butyl cyanoacrylate", Japanese Journal of Radiology, vol. 31, No. 10, Aug. 25, 2013 (Aug. 25, 2013), pp. 685-692.
Khoriaty, Evelyne et al., "Intraoperative anaphylaxis induced by the gelatin component of thrombin-soaked gelfoam in a pediatric patient", Annals of Allergy, Asthma & Immunology, vol. 108, No. 3 , 2012, pp. 209-210.

* cited by examiner

*Primary Examiner* — Michael G. Hartley
*Assistant Examiner* — Lance W Rider
(74) *Attorney, Agent, or Firm* — K&L Gates LLP

(57) ABSTRACT

Provided herein are hemostatic compositions. In one embodiment, the hemostatic composition includes crosslinked polymer microspheres, such as cross-linked gelatin microspheres with pores. In another embodiment, the hemostatic composition comprises an additive such as a wetting agent, a suspending agent, or both. The hemostatic compositions may also include a hemostatic agent such as thrombin, and may include a high concentration of thrombin. The hemostatic compositions may also include plasma. Also provided herein are devices for dispersing said hemostatic compositions in a diluent, and delivering said dispersed hemostatic composition. The hemostatic compositions may also fabricated with a selected geometry as administration suggests.

13 Claims, 8 Drawing Sheets

HEMOSTATIC MICROSPHERES

RELATED APPLICATIONS

This application claims the benefit of U.S. Patent application No. 61/042,156, filed Apr. 3, 2008; and U.S. Patent application No. 61/150,466, filed Feb. 6, 2009, all of which are herein incorporated by reference.

FIELD OF THE INVENTION

This invention relates to hemostatic compositions, such as cross-linked polymers including porous cross-linked gelatin microspheres, that may include hemostatic agents such as thrombin and/or plasma. In certain embodiments, the hemostatic compositions may include doses of thrombin that encompass a range of thrombin concentrations in order to provide for rapid and reliable onset of hemostasis. In particular embodiments, the hemostatic compositions may comprise high doses of thrombin, e.g., 1000 IU/ml or higher, to provide for rapid and reliable onset of hemostasis.

BACKGROUND OF THE INVENTION

Bleeding as a result of surgery or injury may be controlled by passive hemostats and/or hemostatic agents. Passive hemostats control bleeding mechanically, through pressure and absorption, and may be fragmented or otherwise mechanically disrupted powders, gauze, or sponges made from oxidized regenerated cellulose, or cross-linked gelatin. Often, a passive hemostat is combined with an active hemostat, such as thrombin. There remains a need, however, for improved hemostatic compositions, particularly those that render superior clot formation.

DESCRIPTION OF THE DRAWINGS

FIG. 1A is a plot of clot strength with increasing concentrations of microsphere gel. FIG. 1B is a plot of clot time (minutes reaction time) with increasing concentrations of microsphere gel. ♦ IU thrombin/mg dry microspheres; ■ microspheres only; error ±1 IU/mL Thrombin.

FIG. 7A shows data from a rat theminephrectomy model, showing TTH of rThrombin or placebo applied with gelatin matrix. FIG. 7B reflects data from a Rabbit liver injury model indicating TTH of rThrombin or placebo applied with gelatin matrix. FIG. 7C shows data from an A-V shunt graft puncture model, with TTH of rThrombin or placebo administered with gelatin matrix or as a spray.

DETAILED DESCRIPTION OF THE INVENTION

Figure 1A:
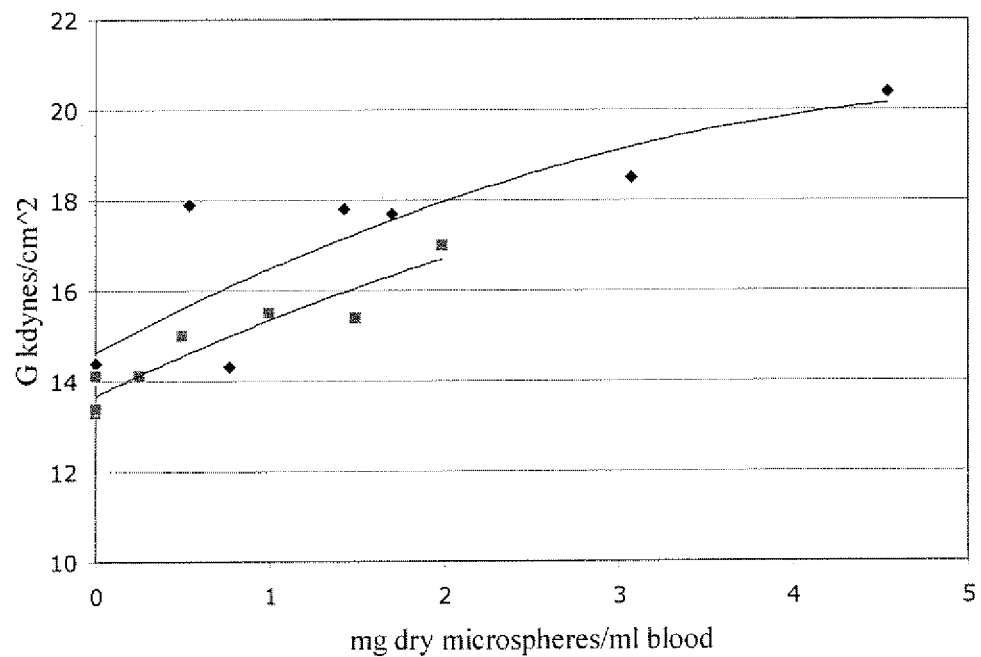
FIGS. 1A and 1B demonstrate that a formulation comprising thrombin and polymer microspheres rehydrated into a gel improves clot strength and shortens clotting reaction time.

It should be understood that this invention is not limited to the particular methodology, protocols, and reagents, etc., described herein and as such may vary. The terminology used herein is for the purpose of describing particular embodiments only, and is not intended to limit the scope of the present invention.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The present invention provides for hemostatic compositions comprising a cross-linked, polymer microsphere. The hemostatic composition may be a cross-linked gelatin microsphere; but collagen, dextran, chitosan, alginate, protein, polysaccharide, polyacrylamide, and other hydrogel compositions may also be used. In a particular aspect, the cross-linked gelatin microspheres may have a diameter from about 50 µm to about 500 µm. In addition, the cross-linked gelatin microspheres may further comprise pores having a pore diameter of about 20 µm. In certain embodiments of the invention, both the microsphere particle size and the pore diameter is optimized to maximize the desired uptake into the microsphere and the release of the hemostat, or sustained application of the hemostat in the hemostatic composition in various bleeding applications. A decrease or increase in particle size or in pore diameter may enable the slow or rapid release of hemostat in the hemostatic composition depending on the application. For example, particle sizes may range from about 10 µm to about 500 µm, inclusive, in typical cross-linked gelatin microsphere. It is understood that within the ranges of particle sizes in the hemostatic microspheres of the present invention that narrower ranges within the 10 to 500 µm can be achieved, such as about 10 to 100 µm, 100 to 200 µm, 100 to 300 µm, 100 to 400 µm, 200 to 300 µm, 300 to 400 µm, 400 to 500 µm, 50 to 150 µm, 150 to 250 µm, 150 to 350 µm, 250 to 350 µm, 350 to 450 µm, each inclusive, and similar incremental ranges between 10 µm and 500 µm. Moreover, smaller pore diameters from 1 µm to 50 µm, inclusive, may be employed, as well as larger pore diameters from 50 to 200 µm, or up to 300 µm, inclusive, in some applications where larger pore diameters are desired. It is understood that within the ranges of pore diameters in the hemostatic microspheres of the present invention that narrower ranges within the 1 µm to 300 µm, inclusive, can be achieved, such as 1 to 50 µm, 50 to 100 µm, 100 to 150 µm, 150 to 200 µm, 200 to 250 µm, 250 to 300 µm, 10 to 60 µm, 20 µm to 70 µm, 30 to 80 µm, 40 to 90 µm, 60 to 110 µm, 70 to 120 µm, 80 to 130 µm, 90 to 140 µm, each inclusive, and similar incremental ranges up to about 300 µm.

Haemostatic agents such as thrombin and/or plasma may be used. In certain embodiments, the hemostatic compositions may comprise thrombin. Such thrombin may be animal- or human-plasma derived, or may be recombinant thrombin such as recombinant human thrombin (rThrombin). Moreover, additional hemostatic agents may be used in addition to thrombin, such as fibrinogen, factor XIII, Protein C, epinephrine, thrombomodulin, factor V, factor VIII, and the like.

Further to this aspect, the hemostatic composition may be mixed with a wetting agent, for example poloxamer or poloxamer 188, polyethylene glycol, or polysorbate. Alternatively, the hemostatic composition may be mixed with a suspending agent such as carboxymethyl-cellulose. The hemostatic composition with or without wetting agent and/or suspending agent may be prepared as a dry powder, or as pre-formed geometries where the hemostatic composition is compressed, dried, chemically bound, or thermally formed into a desired configuration. In a further aspect of this embodiment, an active hemostat, e.g., thrombin, is combined with the diluent used to disperse said cross-linked microsphere prior to administration. In a particular embodiment, the diluent comprises plasma, which may be derived from a patient's own blood. In a further embodiment, the microspheres are suspended in a diluent of sufficient viscosity, adhesiveness and density that application in a non-gravity dependent manner may occur.

Another embodiment provides for a hemostatic composition comprising a cross-linked polymer (e.g., cross-linked gelatin) microspheres and at least one additive. In one aspect, the additive is a wetting agent and/or a suspending agent. The additive may be a wetting agent, such as poloxamer or poloxamer 188, polyethylene glycol, or polysorbate. Alternatively, the additive may be suspending agent, such as carboxymethylcellulose. The hemostatic composition may be a dry powder. In a further aspect of this embodiment, an active hemostat, e.g., thrombin, is combined with the diluent used to disperse said cross-linked polymer microsphere and one or more additives. The diluent may comprise plasma, such as plasma prepared from the subject receiving the hemostatic composition.

The hemostatic composition mixed with additive can comprise a plurality of porous, cross-linked microspheres. The cross-linked gelatin microspheres may be mixed with a wetting agent, such as poloxamer 188, in a weight-to-weight ratio ranging from 60:1 to 3:1 (ratio of gelatin microsphere:poloxamer 188), inclusive. To prepare for application to a target site, the hemostatic composition is easily and substantially homogenously dispersed in an aqueous vehicle, yielding the consistency of a fully-hydrated paste or gel. The hemostatic compositions of the present invention are prepared at the point of use, yet they maintain physical properties to provide syringeability and flowability over extended time periods (e.g., hours).

The present invention also includes methods of making and sterilizing medical devices containing the hemostatic compositions disposed therein.

Another embodiment of the present invention provides for a hemostatic composition carrying a range of thrombin doses from low to high doses of thrombin. More specifically, porous microspheres may be charged with 125 IU to 700 IU thrombin, inclusive; 700 IU to 1,000 IU, inclusive; 1,000 IU; 2,000 IU; or up to 5,000 IU thrombin per mL rehydrated microsphere gel, inclusive. In certain applications porous microspheres may be charged with over 1,000 IU thrombin per mL rehydrated microsphere gel, over 2,000 IU thrombin per mL rehydrated microsphere gel, for example up to 5,000 IU per mL and up to 50,000 IU per mL rehydrated microsphere gel, inclusive. These compositions release a high level of thrombin, yield a homogenous clot, and are especially useful compositions for applications in blood containing a blood-thinner such as aspirin or heparin or an anti-clotting agent such as clopidogrel bisulfate (e.g., Plavix® or other brand).

An alternative embodiment comprises a geometric hemostatic device shaped from a compressed hemostatic composition, that may be applied by common surgical instrumentation or as part of specially designed instrumentation for use in endoscopic, microscopic and robotic hemostatic applications. For example, the porous microspheres may be compressed, dried, chemically bound, or thermally formed into cylindrical shapes that retain their shape and rigidity or that achieve a certain flexibility after wetting. Such shaped compositions are suitable for introduction via an endoscope, and thus serve as a reservoir to thrombin delivery, as well as a firm extension that may be grasped or attached to endoscopic instruments for the simultaneous application of pressure and thrombin. Alternatively, the porous microspheres may be compressed, dried, chemically bound or thermally formed into shapes that conform to surgical anatomical structures that require application of thrombin via a fluid (thrombin) retaining, pressure transmitting substrate. Such shapes could include annular shapes and semi-annular shapes for placement around vascular anastomoses of various sizes. They may also be shaped to conform to predictable surgically-induced cavity defects, such as those arising from breast "lumpectomy", or other surgically-induced cavity defects.

A further embodiment provides for a hemostatic composition in a delivery device for application of said hemostatic composition to a site of interest. In one aspect of this embodiment the delivery device is a syringe. In a further aspect of this embodiment, said syringe is attached to a delivery tip.

A further embodiment provides for a method of applying a hemostatic composition to a target site with the objective of reducing bleeding. In one aspect of this embodiment, the hemostatic composition is applied to a target site (bleed) using a piece of gauze. In this aspect, the hemostatic composition is applied to the gauze and then the gauze and the hemostatic composition are applied to a target site, thus bringing the hemostatic composition in contact with the bleed. The method of the present embodiment provides for a stronger clot when compared to blood alone.

In another aspect the hemostatic composition is applied to a target site via its dispensing from a syringe. In this aspect, a syringe is loaded with a hemostatic composition and the syringe is directed towards the target site. The hemostatic composition is then extruded from the syringe to the target site. Optionally, a piece of gauze is then applied over the hemostatic composition at the target site, whereupon mechanical pressure is applied by a surgeon. In a further aspect of this embodiment, a syringe attached to a tip is loaded with a hemostatic composition and the syringe and tip are directed towards the target site. Hemostatic composition is then extruded from the syringe to the target site. Tips are useful, for example, when the target site is at a location that is not readily accessible to a syringe alone. Such places include target sites that are deep within a cavity, are partially obstructed by an organ, or others. Tips are also useful for controlling the size of the extruded hemostatic composition.

For example, a tip can be useful allowing the user to extrude a continuous line of hemostatic composition to a lengthy bleed site. Optionally, a piece of gauze is then applied over the hemostatic composition at these target sites.

An embodiment of the present invention provides for an efficacious, flowable hemostatic composition, which may comprise a cross-linked gelatin microsphere that exhibits minimal but rapid and complete swelling; minimal "stickiness;" and acceptable syringeability upon dispersion in aqueous solution. More specifically, the embodiment provides for a significantly porous polymer microsphere, e.g., cross-linked gelatin microsphere, wherein the pores increase the particle surface area, thereby increasing contact activation at the procoagulant surface to facilitate hemostasis. Further, the pores can entrap an active hemostat, such as thrombin, thereby increasing the retention of the active hemostat at the application site. Indeed, the hemostatic composition may carry a higher dose of thrombin than has been described previously. These cross-linked gelatin microspheres are an improvement over the fragmented hydrogels currently used as passive hemostats.

Particular embodiments also provide for porous microspheres that are not administered in powder form. Instead, these porous microsphere, hemostatic compositions are bound into geometries that replicate current gelatin sponge conformations (rectangular, hexahedron shapes) or that include any and all other potential conformations. For example, porous microspheres may be compressed, dried, chemically bound, or thermally formed into cylindrical shapes that retain their shape and rigidity or that achieve a certain flexibility after wetting and are suitable for introduction via an endoscope, and thus serves as a reservoir for thrombin delivery as well as a firm structure that may be grasped or attached to endoscopic instruments for the simultaneous application of pressure and thrombin. Alternatively, the porous microsphere hemostatic composition may be compressed, dried, chemically bound or thermally formed into shapes of all kinds that conform to surgical anatomical structures that require application of thrombin via a fluid (thrombin) retaining, pressure transmitting substrate. Such shapes could include annular shapes and semi-annular shapes for placement around vascular anastomoses of various sizes, as well as shapes that conform to predictable surgically-induced cavity defects such as those arising from breast "lumpectomy" or other surgically-induced cavity defect.

The efficacy and usability of cross-linked gelatin powders are dependent on the fraction and degree of cross-linking, where the fraction of cross-linked gelatin out of the total gelatin describes the fraction of gelatin insoluble at body temperature (37° C.) and the degree (also referred to as extent) of cross-linking is a measure of the amount of cross-links within 37° C. insoluble, cross-linked gelatin. If the fraction cross-linked is too low, soluble gelatin present in the dispersed gelatin matrix reduces the concentration of suspended particles responsible for the hemostatic effect that can lead to reduced efficacy marked by bleed-through. Also, these preparations can have reduced efficacy because the soluble gelatin can render the dispersed product "stickier," which leads to re-bleeding following removal of gauze or other materials often used to aid in pressure application to facilitate hemostasis. If the degree of cross-linking is too high, the cross-linked gelatin can be rendered too hydrophobic to allow for easy and homogeneous dispersion in aqueous solutions, thereby reducing usability (i.e., syringeability). If the degree of cross-linking is too low, the cross-linked gelatin can be too absorptive leading to extended swelling times with varied consistency over time subsequent to dispersion. Excessive swelling after application of partially hydrated absorbents can also potentially lead to serious adverse reactions such as paralysis and nerve damage if hemostats are used in, or in proximity to foramina in bone, areas of bony confine, the spinal cord, and/or the optic nerve and chiasm.

The degree and extent of gelatin cross-linking is also affected by ionizing radiation (i.e., e-beam or γ-irradiation) often used to terminally sterilize medical devices. Although the ionizing radiation dose required for terminal sterilization is dependent on the product bioburden prior to irradiation, a typical sterilizing dose of γ-irradiation for medical devices is 25 kGy; a 25 kGy target γ-irradiation dose often exposes the products to a range of 15 kGy to 35 kGy. The fraction cross-linked and degree of cross-linking can be reduced when cross-linked gelatin is irradiated as a dry powder. The degree and extent of gelatin cross-linking can be increased, however, when cross-linked gelatin is irradiated as hydrated dispersions. As such, the properties, such as solubility, hydrophobicity and/or swelling, of the terminally sterilized cross-linked gelatin are dependent on the degree and extent of cross-linking prior to irradiation, as well as the form that is irradiated (i.e., hydrated dispersion or dry powder). Irradiating cross-linked gelatin that has a limited fraction cross-linked and degree of cross-linking as a hydrated dispersion could lead to intra-batch variability due to the range of irradiation exposure (e.g., 15 kGy to 35 kGy).

Ideally, a gelatin cross-linking process produces a product with a sufficient degree and extent of cross-linking so that any changes induced by exposure of a dry powder to a range of ionizing radiation doses (e.g., 15 kGy to 35 kGy) are inconsequential with regard to solubility, hydrophobicity, and/or swelling. Gelatin can be cross-linked using a dehydrothermal or chemical process that utilizes cross-linking agents such as glutaraldehyde or hexamethylene diisocyanate. Cross-linked gelatin having low fraction of cross-linked gelatin and degree of cross-linking have significant increases in solubility, swelling, and "stickiness" induced if irradiated as a dry powder because the degree and extent of cross-linking is reduced. Irradiating cross-linked gelatins with a limited fraction and degree of cross-linking as a hydrated paste leads to intra-batch variability in solubility, hydrophobicity, and stickiness due to product exposure over an irradiation dose range (i.e. 15 kGy to 35 kGy).

Existing commercial cross-linked hydrogel products are supplied either as a dry powder or a partially hydrated paste intended for administration after dispersion in an appropriate amount of aqueous vehicle. These powders are formed by mechanical disruption of cross-linked matricies, such as absorbable gelatin sponges, U.S.P. (e.g., GELFOAM®, Pfizer, Inc. or SURGIFOAM™, Ethicon, Inc.), or the cakes that are Rained during typical chemical or dehydrothermal cross-linking treatment (see, e.g., U.S. Pat. No. 6,063,061; U.S. Patent application pub. No. 2003/0064109). These cross-linked hydrogels are most typically gelatin based hydrogels, however, collagen, dextran, chitosan and other compositions are also used, as is know to one skilled in the art.

Hydrogel-based hemostatic compositions may be administered dry, partially hydrated, or fully hydrated. In the fully hydrated state, the hydrogel can not absorb further fluid, and is fully swollen in size. In contrast, a dry or partially hydrated hydrogel composition has excess adsorptive capacity. Upon administration, dry or partially hydrated hydrogel will absorb fluid leading to a swelling of the gelatin matrix in vivo. Excessive swelling after application can potentially lead to serious adverse reactions, such as paralysis and nerve damage if hemostats are used in, or in proximity to, foramina in bone, areas of bony confine, the spinal cord, and/or the optic nerve and chiasm. Hence, swelling of dry or partially hydrated hydrogel should be considered in the context of administration.

The ideal hemostatic composition has at least one the following properties: it is compatible with active hemostats, such as thrombin; it has limited aqueous solubility of the hemostatic gelatin matrix; it exhibits minimal changes in efficacy and usability after exposure to a wide range of ionizing radiation (15 kGy to 35 kGy) sufficient to yield a terminally-sterilized product; it shows rapid and complete swelling when dispersed in aqueous vehicle; it is effective when administered fully-hydrated; it has acceptable syringeability, allowing complete dispensing of a homogeneous dispersion from a syringe (or delivery device) with minimal force; it contains significant porosity; it has a short resorption time after administration (less than one year, or less than six months); its particle shape and size facilitates flow properties as both dry powder and dispersed suspension (e.g., gel).

In a further embodiment, the present invention utilizes a porous, cross-linked gelatin hydrogel microsphere combined with a wetting agent and/or a suspending agent resulting in a flowable cross-linked composition that exhibits minimal but rapid and complete swelling, minimal stickiness and improved syringeability upon dispersion in aqueous solution. The chemically cross-linked microsphere may be manufactured by an emulsion process that is specifically designed to produce approximately spherical microparticles and introduce pores of an average size of about 20 µm and yields a microsphere product of defined particle size range (about 50 µm to about 500 µm). The microspheres can be manufactured according to U.S. Pat. No. 7,404,971, U.S. Pat. No. 4,935,365, U.S. Pat. No. 5,015,576. Microspheres are also available commercially, for example, CultiSpher®-S macroporous gelatin microcarrier microspheres (Celltrix, Malmo, Sweden; Percell Biolytica, Åstorp, Sweden). Hemostatic efficacy has been established as a fully hydrated dispersion in non-clinical models.

One advantage as a hemostat of the cross-linked gelatin microsphere powder prepared by an emulsion process containing pores (versus microsphere powder without pores) of a defined particle size range (that excludes fine and course particles) has been established using non-clinical bleeding models. Another advantage of the cross-linked gelatin microsphere process is to yield a dry powder that is resistant to changes over a range of γ-irradiation doses (15 kGy to 35 kGy) compared with cross-linked gelatins in the art, in terms of those properties necessary for efficacy of a flowable passive hemostat (i.e., solubility, hydrophobicity, swelling). The spherical particle shape and defined size distribution also facilitates powder flow properties that aid manufacturing (e.g., filling of the dry powder into a delivery device) and dispersion in aqueous vehicles. Although the porous microspheres of the current invention provide the previously discussed advantages as a hemostat, the particles have a "sponging-out" effect wherein aqueous solution is removed from a hydrated dispersion when said dispersion is used in a delivery device that relies upon mechanical force for delivery of said hydrated dispersion. For example, when the porous, cross-linked microspheres are dispersed in an aqueous solution and the delivery device is a syringe, the mechanical force applied to the syringe plunger causes a sponging-out of the aqueous solution disproportionately to the porous, cross-linked microsphere. As a result, the initially dispersed material has a more dilute consistency than does the later dispersed material. Moreover, the later-dispersed material may become so dry from the sponging-out effect that this later material will not disperse from a syringe with reasonable force.

The sponging-out effect is ameliorated, however, by inclusion of wetting agents (e.g., poloxamer 188, polyethylene glycol 3350, polysorbate 20 or polysorbate 80) and/or suspending agents (e.g., carboxymethyl-cellulose) as additives. The wetting agent may be mixed with a porous, cross-linked gelatin microsphere in an appropriate ratio dependant on the agent used. Regarding poloxamer-188, for example, a weight-to-weight ratio of 60-3:1 (cross-linked gelatin:additive) is effective. Similarly, the suspending agent may be mixed with a porous, cross-linked gelatin microsphere in weight-to-weight ratio of 60-3:1 (cross-linked gelatin:additive). If a mixture of wetting agent and suspending agent are mixed with the porous, cross-linked gelatin microsphere, the wetting agent plus suspending agent are mixed with a porous, cross-linked gelatin microsphere in an appropriate ratio. The suspending/wetting agents may also be introduced via the vehicle used to disperse the microspheres, as could be done for the polysorbates. The combination of cross-linked gelatin microsphere powder and additive ensures the desirable properties of the flowable passive hemostat (i.e., homogeneity of dispersions, minimal extrusion force) are retained for extended time periods (hours). The described formulation is also compatible with thrombin.

In several embodiments of the present invention, the hemostatic composition includes thrombin. As used herein, "thrombin" denotes the activated enzyme, also known as alpha-thrombin, which results from the proteolytic cleavage of prothrombin (factor II). Thrombin can be prepared by a variety of methods known in the art, and the term "thrombin" is not intended to imply a particular method of production. Both human and non-human thrombins can be used within the present invention. Thrombin is used medically as a hemostatic agent and as a component of tissue adhesives. Human and non-human (e.g., bovine) thrombins are prepared according to methods known in the art. Purification of thrombin from plasma is disclosed by, for example, Bui-Khac et al., U.S. Pat. No. 5,981,254. Purification of thrombin from plasma fractions, such as Cohn fraction III, is disclosed by Fenton et al., 252 J. Biol. Chem. 3587-98 (1977). Recombinant thrombin can be prepared from a prethrombin precursor by activation with a snake venom activator as disclosed in U.S. Pat. No. 5,476,777. Thus, the thrombin may be a recombinant thrombin. The amount of the recombinant thrombin in the formulation may be between 3000 NIH (National Institutes of Health) Units and 30,000 NIH Units of recombinant thrombin, inclusive, or 5000 NIH Units of recombinant thrombin. In this aspect, the thrombin may be provided in the kit as a lyophilized powder (see, e.g., U.S. Pat. No. 7,473,543). This lyophilized powder can be reconstituted using a diluent, including a diluent comprising plasma.

Figure 4A:
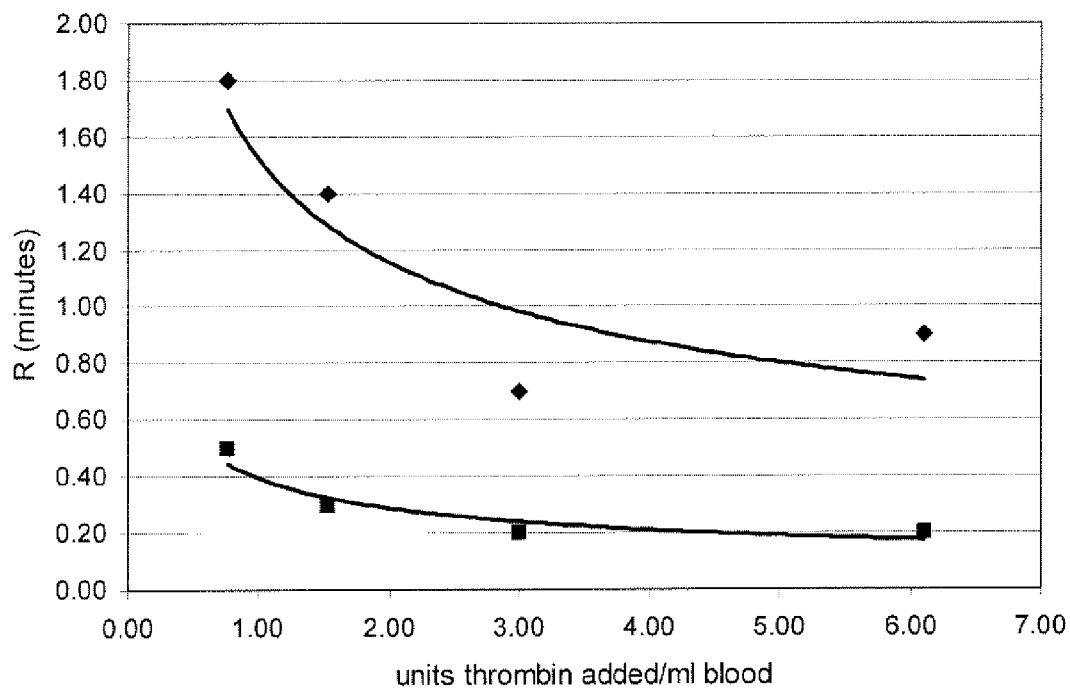
FIGS. 4A and 4B graphically present expanded views of non-heparin plots. When thrombin is mixed directly with blood the clot is not homogenous because of rapid clot formation. The addition of thrombin to the gelatin beads prior to mixing with blood or liquid allows better mixing to occur and improves clot reaction time and clot strength. ♦ thrombin mixed with 1.2 mg gelatin beads; ■ thrombin mixed directly with blood.
Figure 4B:
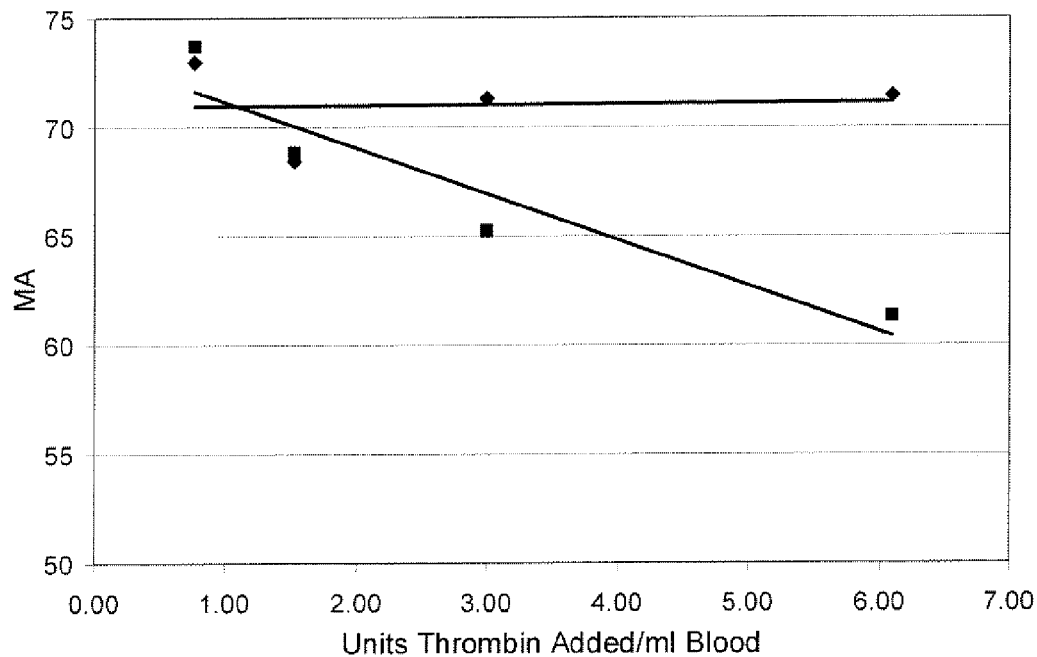

In another embodiment of the invention, when the thrombin is added to dry microsphere gel and then introduced into blood, the rate of clot formation is increased, indicating that the clot kinetics is slower than when thrombin is added directly into blood (FIG. 4A). When combined with the cross-linked polymer microspheres of the present invention, thrombin also yields better clot strength (FIG. 4B). Without the microsphere gel, the clot strength declines with increasing thrombin, whereas the thrombin plus microsphere gel maintains clot strength. In this regard, thrombin may be included in the hemostatic composition of the present invention at a concentration of about 1000 IU/mL. This data also supports that higher thrombin concentrations may be used in haemostatic compositions containing microsphere gels. Without being bound by theory, passive diffusion of the thrombin from the high-thrombin-dose hemostatic composition may aid in the formation of the homogenous, strong clot. The importance of this formulation is readily apparent in blood that has been treated with a thinner or anti-clotting agent such as aspirin, heparin, or clopidogrel bisulfate. In the case of such treated blood, the high-dose thrombin microspheres hemostatic composition is able to deliver ten-times the thrombin found in normal blood and yield a normal blood clot. The importance of this formulation is also readily apparent in surgical or other bleeding applications where formation of the homogenous, strong, clot is desirable in the absence of such thinner or anti-clotting agent.

As used herein, "matrix" denotes a mixture containing at least microspheres and a hemostatic agent. A matrix may or may not also contain a wetting agent. For example, as used in some examples herein, a matrix includes cross-linked gelatin microspheres, thrombin (e.g., rThrombin) as a hemostatic agent and a poloxamer such as poloxamer 188. It is understood that a matrix may contain different mixtures of microspheres, a hemostatic agent, and one or more wetting agents as described herein.

As used herein, "dispersion" denotes a mixture containing at least two phases (for example, a mixture containing a solid and a liquid phase). Depending on the viscosity of a dispersion, it may be considered a suspension or a paste. Microspheres in the hemostatic compositions of the present invention can be dispersed in an aqueous vehicle, including an aqueous vehicle comprising plasma.

Since the 1940s, thrombin has been used during surgical procedures as a topical hemostatic agent to speed time to hemostasis (TTH) and improve visualization of the surgical field, and for use in procedures such as including use in burn patients undergoing debridement and skin grafting (Bishop et al., 32(S1) Semin. Thromb. Hemost. 86-97 (2006); Lundblad et al., 91(5) Thromb. Hemost. 851-60 (2004)). The safety and efficacy of 1000 IU/mL of topical thrombin was recently confirmed in human clinical trials (Chapman et al., 205(2) J. Am. Coll. Surg. 256-65 (2007); Doria et al., 24(3) Curr. Med. Res. Opin. 785-94 (2008)), but human clinical trials have not compared the effects of differing concentrations of topical thrombin on hemostatic efficacy. The critical nature of thrombin concentration in fibrin clot formation has been demonstrated in a number of in vitro settings, however, indicating that clots formed in the presence of high concentrations of thrombin have more tightly packed fibrin strands.

Indirectly, variations in time to hemostasis in vivo may indicate relative effects of topical thrombin concentration on clot integrity. A recent evaluation in a porcine liver injury model of human thrombin plus gelatin sponge at 125 IU/mL showed improved activity over saline plus gelatin sponge (Adams et al., J. Thromb. Thrombolysis [0929-5305] (Jul. 16, 2008)). Even with a liberalized definition of hemostasis (limited oozing was also a permitted endpoint), limited accumulative hemostasis was observed after the first 3-minute time point. There were also a significant number of sites rebleeding during the 12-minute evaluation period, however, pointing strongly to concentration limited hemostatic effect. Those observations raise the question of whether there is a difference in onset of hemostasis and clot integrity between the standard 1000 IU/mL and the lower 125 IU/mL application (Adams et al., 2008).

Based on these observations, the adoption of 1000 IU/mL thrombin concentration may have evolved in clinical practice because of observed efficacy in a range of clinical settings that included both pathologic and pharmacologic clotting derangements. It stands to reason that the potency of the thrombin enzyme in coagulation would enable lower concentration of topical thrombin to be effective in some, but not all clinical settings. For example, when high thrombin is added directly into blood by standard pipetting techniques the fibrinogen is converted to fibrin faster than mixing can occur, which results in a non-homogenous clot. Hence, to test the effect of thrombin concentration on time to hemostasis (TTH) under varying conditions of pharmacologic anticoagulation and platelet impairment, a range of thrombin concentrations were evaluated in a model of brisk arterial anastomotic bleeding in rabbits. Parallel evaluations of clot viscoelastic properties were performed by modified thromboelastography. To examine whether clot integrity was of potential clinical significance, clot burst at the site of bleeding was evaluated.

Thrombin concentration during fibrin clot formation determines clot integrity at the time of hemostasis. Numerous factors work to reduce both endogenous and exogenous thrombin concentration at the bleeding wound interface: removal and dilution by hemorrhagic blood flow, rapid binding to inhibitors such as ATIII, entrapment in developing thrombus, and mechanical removal by sponge and/or irrigation. Whether topical thrombin is applied or not, surgeons rely on intraoperative gross evaluations of hemostasis as predictors of whether hemostasis will be durable after wound closure. As a practical matter, the consequences of inadequate clot structure are observed when rebleeding or hematoma formation occurs. When hemostasis is delayed, coagulability is usually assessed by PT, PTT, and platelet count with or without platelet function measurements. In addition, thromboelastography (TEG), an ex vivo analysis of time dependent viscoelastic changes during clot formation may be performed as a means for rapidly detecting pathologic derangements in clotting. These laboratory assessments may not directly correlate with intraoperative bleeding severity nor do they predict response to surgical intervention due to the many variables influencing clot formation in the wound. Not all of these variables are understood in real time, with the predictable result that current depictions of the fibrin polymerization and platelet incorporation during clot formation are highly stylized.

Multiple in vitro experiments have indicated that thrombin concentration is the most critical factor during fibrin clot formation, and clots formed in the presence of high concentrations of thrombin have more tightly packed fibrin strands (Blomback et al., 997 (1-2) Biocim. Biophys. Acta 96-110 (1989); Blomback et al., 75(5) Thromb. Res. 521-38 (1994); Wolberg, 21(3) Blood Rev. 131-142 (2007)). In addition, normal platelet function is required for physiologic clot initiation. One group has described the thrombin concentration dependency of hemostasis in a series of controlled in vivo bleeding models. Exogenous rThrombin was effective in achieving hemostasis in an in vivo rabbit model for hepatic bleeding related to surgery, at doses between 500 IU/mL and 2000 IU/mL (Heffernan et al., 47(1) Regul. Toxicol. Pharmacol. 48-58 (2007)). In this model, rThrombin was effective in stopping bleeding in a dose-dependent manner when applied with gauze pads. A similar rabbit in vivo model used rThrombin at concentrations from 100 IU/mL to 2000 IU/mL with either gauze sponges or absorbable gelatin sponges, and also showed reduced time to hemostasis (TTH) which was dependent on the rThrombin dose (Meehan & Bolton, 121(2) J. Surg. Res. 323 (2004)).

The rabbit in vivo model presented herein replicates vascular anastomotic bleeding with a rabbit arterial venous (AV) grafts model. This model was used to evaluate 31.25 IU/mL, 62.5 IU/mL, 125 IU/mL, and 1000 IU/mL rThrombin in combination with absorbable gelatin sponge, USP, and the effect on TTH. In other assays, TTH was evaluated using two concentrations of rThrombin, 125 IU/mL and 1000 IU/mL, as hemostatic agents in combination with an absorbable gelatin sponge, USP, in rabbits that had been pretreated with clopidogrel bisulfate, heparin, or both. In animals treated with heparin only, both rThrombin concentrations accelerated hemostasis. Notably, the standard error around the TTH achieved by 125 IU/mL was much broader than that of the 1000 IU/mL treated animals. In clopidogrel bisulfate-treated animals, rThrombin at 1000 IU/mL achieved hemostasis at the same time point as in the heparin-only-treated animals. In contrast, clopidogrel bisulfate inhibition of platelet function was not overcome by the application of 125 IU/mL rThrombin. The reason for this disparity in efficacy is not intuitively obvious, and concentration-dependent thrombin reversal of the effects platelet inhibition on coagulability has not been reported. This lends credence to the widespread use of topical thrombin preparation in vascular and cardiac surgery; because thrombin at 1000 IU/mL speeds hemostasis over the full spectrum of clinical bleeding challenges.

An active test of clot integrity was performed by clamping the graft following the achievement of hemostasis (clot burst testing). The results suggest that there is another effect of thrombin concentration that needs to be considered: clot stability. This provocative test measures the adhesiveness of the clot boundary to the PTFE graft material as well as platelet force development. Platelet force development is a process of thrombus maturation in which platelets contract with the consequence of increasing fibrin strand density thus ensuring that a sudden spike in pressure does not lead to clot failure. Pharmacologic and mechanical inhibition of platelet function has been associated with increased bleeding in humans after cardiopulmonary bypass (Greilich et al., 105 (6) Thromb. Res. 523-29 (2002)). In this light, it is likely that the rebleeding wounds evaluated in the porcine hepatic bleeding model at 12 minutes rebled secondary to reduced clot strength and density. Notably, there was no reasonable means by which clot burst could have been studied in that model, because hepatic bleeding is generally low pressure, venous bleeding.

Additionally, a thromboelastograph technique (TEG) was used in vitro to examine clot strength using samples in vitro from rabbits in the in vivo AV shunt experiments. Blood clots have both viscous and elastic properties, and the thromboelastograph has been used to measure the clot strength (elastic shear modulus) of clotting blood, and has been demonstrated to measure elastic properties independent of viscosity (Chandler, 21(S4) Seminars Thromb. & Hemost. 1-6 (1995)). Because exogenous thrombin causes almost immediate clotting, it was necessary to alter the conditions typically used for TEG experiments so that the reaction could be slowed. The in vitro TEG experiments were also used to demonstrate the effect various anticoagulants had on clot strength, and the interaction of various concentrations of rThrombin when anticoagulants were present. Although the TEG experiments require rThrombin concentrations that cannot be compared directly with the concentrations of rThrombin used in the rabbit AV shunt model, the data confirm the concentration dependent reversal of the effects of clopidogrel bisulfate platelet dysfunction on clot formation.

The present work evaluates the effects of thrombin concentration on three areas of clinical hemostasis pertinent to every surgical practice: time to cessation of bleeding across a range of pharmacological coagulation inhibition, clot strength and resistance to clot disruption. The observation that rThrombin at 1000 IU/mL negates the effects of clopidogrel bisulfate on time to hemostasis has significant implications for clinicians. Clopidogrel bisulfate irreversibly inhibits ADP receptors on platelets and there is a wide variety of opinion regarding the timing of discontinuation clopidogrel bisulfate prior to surgery. In patients with high risk of perioperative MI, it has been argued that stopping clopidogrel bisulfate may affect the incidence of adverse cardiac events. Thus, an ever increasing percentage of patients are coming for urgent, emergent and elective procedures with significant clopidogrel bisulfate platelet inhibition. The ability of 1000 IU/mL topical rThrombin to negate the impact of clopidogrel bisulfate platelet inhibition on time to hemostasis may mitigate the bleeding risks that result from those changes in surgical population.

Additionally, surgical treatment of coagulation impaired patients has evolved over time. In this study, the thromboelastographic confirmation of the thrombin concentration dependence on clot strength further supports the idea that fibrin clot density is a function of available thrombin concentration. Consequently, durable hemostasis was in all likelihood a key driver for the evolution of thrombin 1000 IU/mL as the standard concentration for most surgical applications.

Moreover, the observation that clots formed in the presence of the higher thrombin concentration were more resistant to clot disruption is important as evidence of the differences in clot structure and maturation that occur at differing thrombin concentrations. Persistent hemostasis that resists the stresses of the early recovery period is a desirable outcome for all surgery. Thus, the use of topical rThrombin at 1000 IU/mL is reasonable as a standard of care. Although both 125 IU/mL or 1000 IU/mL rThrombin will shorten the time to onset of hemostasis when applied with absorbable gelatin sponge, the superior clot structure and maturation occurring at the higher thrombin concentrations suggest that higher concentrations of thrombin may perform better in a clinical setting. rThrombin will consistently shorten time to hemostasis over a range of clinical conditions that mimic the current surgical population, however, although the current use of thrombin 1000 IU/mL is the standard of care for topical hemostasis, use of higher concentrations of thrombin in such applications may be justified.

More specifically, as detailed in the Examples below, a modified, heparinized rabbit arterio-venous (AV) shunt preparation was selected to model vascular anastomotic bleeding. Standardized, polytetrafluoroethylene (PTFE) arterial venous grafts were punctured with a suture needle, immediately wrapped with a thrombin or placebo containing absorbable gelatin sponge, USP, and covered by gauze sponges applied with continual pressure. Bemostasis was assessed using a standardized procedure at regular intervals. In the first set of experiments (heparin only), an absorbable gelatin sponge, USP, was randomly combined with saline, 31.25 IU/mL, 62.5 IU/mL, 125 IU/mL, or 1000 IU/mL of rThrombin, and time to hemostasis (TTH) was assessed by a blinded observer. In a similar second set of experiments (heparin plus clopidogrel bisulfate), AV shunts were inserted and treatment was randomized to placebo, 125 IU/mL or 1000 IU/mL rThrombin, in combination with the absorbable gelatin sponge, USP followed by blinded TTH assessment. In preparations that achieved hemostasis, binary clot burst challenges were performed at 5 minutes by rapid clamping of the distal AV graft. Determination of rThrombin concentration effect on clot viscoelastic strength was obtained by serial evaluations of ex-vivo samples using thromboelastographic (TEG) methods.

In the rabbit AV shunt model, increasing concentrations of rThrombin decreased TTH in a dose dependent manner. When rabbits were pretreated with clopidogrel bisulfate, TTH was significantly lower when 1000 IU/ml, of rThrombin was used in conjunction with an absorbable gelatin sponge, as compared to 125 IU/mL of rThrombin. Furthermore, TTH in the presence of 1000 IU/mL rThrombin was highly reproducible, while TTH at the lower concentration varied widely. The clots formed by the 1000 IU/mL of rThrombin were also less likely to rupture during the clot burst assessment than those formed in the presence of 125 IU/mL of rThrombin. In addition, TEG measurements demonstrated that the rate of clot formation and the strength of clots formed in vitro were dependent on the concentration of rThrombin, particularly in the presence of anticoagulants such as clopidogrel bisulfate.

Thus, in an animal model designed to mimic clinical coagulation dysfunction, topical rThrombin 1000 IU/mL provided rapid, reliable onset of hemostasis when compared to rThrombin 125 IU/mL. The paradigm that thrombin concentration is the key determinant of time to onset of hemostasis and clot strength holds true even in the presence of significant heparinization and potent platelet inhibition.

In another embodiment, the hemostatic composition is provided in a kit, wherein said kit further comprises one or more of; a first syringe, a second syringe, a syringe tip, a diluent, an additive, and thrombin. Optionally, the kit also includes materials suitable for the use of patient plasma in or as the diluent. In an aspect of this embodiment, the hemostatic composition is present within the barrel of said first syringe. The hemostatic composition may comprise a cross-linked gelatin microspheres and is present within the barrel of said syringe as a dry powder. Alternatively, the hemostatic composition is cross-linked gelatin microspheres and is present within the barrel of said syringe as partially or fully hydrated paste or gel. In a further aspect of this embodiment, the hemostatic composition is mixed with an additive and is present within the barrel of the first syringe. Some of the hemostatic composition may be cross-linked gelatin microspheres mixed with an additive, and is present within the barrel of the syringe as a dry powder. Alternatively, the hemostatic composition is a cross-linked gelatin microspheres and is mixed with as additive are present within the barrel of said syringe as partially or fully hydrated paste or gel. As is used herein, powdered hemostatic compositions having a moisture content below 20% by weight are considered dry powders.

In another aspect of this embodiment, there is provided a hemostatic composition mixed with an additive. The hemostatic composition may be a cross-linked gelatin microsphere. In this aspect, said cross-linked gelatin microspheres have a diameter from about 50 μm to about 500 μm. In addition, the cross-linked gelatin microspheres may further comprise pores, and the pores may have a pore diameter of about 20 μm. Further to this aspect, the hemostatic composition is optionally mixed with an additive that is a wetting agent such as poloxamer or poloxamer 188, polyethylene glycol, or polysorbate. Alternatively, the hemostatic composition is mixed with an additive that is a suspending agent such as carboxymethylcellulose. The hemostatic composition with or without wetting agent and/or suspending agent may be a dry powder.

In a further aspect of this embodiment provides for a hemostatic composition mixed with an additive wherein said hemostatic composition is a cross-linked polymer and said additive selected from the group consisting of a wetting agent, a suspending agent, and both a wetting agent and a suspending agent, cross-linked polymer is gelatin; however collagen, dextran, chitosan, alginate and other compositions may also be used. The gelatin may be dehydrothermally cross-linked, or chemically cross-linked, or cross-linked via other means such as irradiation. The cross-linked polymer can be in any shape, such as a cross-linked gelatin microsphere, a cross-linked gelatin microsphere further comprising pores having a diameter from about about 50 μm to about 500 μm, inclusive, a cross-linked gelatin microsphere having a diameter from about about 50 μm to about 500 μm, inclusive, and further comprising pores and said pores having a pore diameter of about 20 µm. The hemostatic composition may be formulated into a dry powder. The additive may be a wetting agent such as poloxamer or poloxamer 188. Alternatively, the additive may be a suspending agent such as carboxymethylcellulose. Cross-linked polymers mixed with additive include but are not limited to those described in U.S. Pat. No. 7,404,971, U.S. Pat. No. 6,063,061, U.S. Pat. No. 4,935,365, U.S. Pat. No. 5,015,576; U.S. Patent applications pub. No. 20050287215, No. 20030064109; CultiSpher®-G and CultiSpher®-S porous gelatin microcarriers (Celltrix, Malmo, Sweden; Pereell Biolytica, Åstorp, Sweden).

In a further aspect of an embodiment, the kit contains a second syringe for containing a diluent, such as saline. Other diluents include calcium chloride diluents, and others as are known in the art. In this aspect, the diluent can be pulled from a diluent container into a syringe by the user. Allowing users to pull diluent into a syringe allows the user to control the amount of diluent used to disperse the hemostatic composition, and thus, control the consistency of a subsequent paste. Alternatively, the second syringe can be packaged within said kit with diluent within the barrel. Thus, the second syringe may be pre-loaded with diluent.

In a further aspect of the kit embodiment, the kit contains thrombin. As noted above, "thrombin" denotes the activated enzyme, also known as alpha-thrombin, which results from the proteolytic cleavage of prothrombin (factor II). Thrombin can be prepared by a variety of methods known in the art, and the term "thrombin" is not intended to imply a particular method of production. In this aspect, the thrombin may be provided in the kit as a lyophilized powder (see, e.g., U.S. Pat. No. 7,473,543). This lyophilized powder can be reconstituted using said diluent. For example, the diluent is applied from said second syringe onto said lyophilized thrombin. This can be done by adding said diluent directly into a vial containing lyophilized thrombin, or both the diluent and the lyophilized thrombin may be combined in a separate container. The diluent may include or consist entirely of plasma. In this aspect, then, the kit can also contain a mixing bowl. Means of mixing thrombin are known to those of ordinary skill in the art.

In a further aspect of the embodiment, the first syringe that contains the hemostatic composition, and optionally an additive, and the second syringe that contains diluent, and, optionally, thrombin, are connected and the content of these two syringes are passed back and forth until the cross-linked gelatin microspheres is fully dispersed within the diluent. The first and second syringes are connected with an adapter, wherein the adapter contains leur threads complementary to the leur threads of the syringes. Alternatively one of syringes has a leur thread that is complementary to the other syringe, thus the two syringes will connect directly using complementary leur connections. This allows for mixing of a hemostatic composition with diluent by connecting said syringes at the leur connections and passing the contents back and forth between the two syringe barrels by applying alternating force to their respective plungers until a desirable dispersion of said hemostatic composition is achieved. The hemostatic composition may be dry before mixing with the diluent, though partially hydrated and even fully hydrated hemostatic compositions can be mixed with diluent. The resulting dispersed hemostatic compositions can be partially hydrated to greater than fully hydrated, depending on the user's preference.

One of the syringes should be sufficient to contain and dispense the dispersed hemostatic composition. Thus, the syringe needs to have a sufficient barrel capacity. Following mixing of the hemostatic composition with diluent using said first and second syringes, the dispersed hemostatic composition are pushed to a single of the two syringes. Large volumes of dispersed hemostatic composition will require that said syringe have a barrel length and width to both accommodate the dispersed hemostatic composition without making the barrel so long that a user cannot easily hold said syringe and depress its plunger with one hand. A syringe will typically contain at least 5 cc, such as at least 8 cc, or at least 12 cc.

The syringe should be durable to withstand the necessary force for extruding a hemostatic composition from its barrel lumen. When the hemostatic composition is, for example, a cross-linked gelatin microsphere without additive, there is a sponging out effect that makes it difficult to expel the later volumes of dispersed hemostatic composition from a syringe. The plunger must be durable enough to withstand this force. Additive alleviates the sponging-out effect, and thus alleviates the amount of force applied to a plunger to extrude the hemostatic composition.

Thus, the hemostatic composition may be mixed with an additive. Sterile hemostatic compositions mixed with an additive include cross-linked polymers. Cross-linked polymers that can be mixed with an additive include, but are not limited to those described in U.S. Pat. No. 7,404,971, U.S. Pat. No. 6,063,061, U.S. Pat. No. 4,935,365, U.S. Pat. No. 5,015,576; U.S. Patent applications pub. No. 20050287215, No. 20030064109; Cultispher®-G or Cultispher®-S macroporous gelatin microcarriers (Celltrix, Malmo, Sweden; Percell Biolytica, Åstorp, Sweden). The hemostatic composition mixed with additive comprises a plurality of porous, cross-linked microspheres. The cross-linked gelatin microspheres may be mixed with a wetting agent, and optionally a poloxamer, such as poloxamer 188, in a weight-to-weight ratio ranging from 60:1 to 3:1 (ratio of gelatin microsphere: poloxamer 188). To prepare for application to a target site, the hemostatic composition is easily and substantially homogenously dispersed in an aqueous vehicle, yielding the consistency of a fully-hydrated paste.

The additive and the hemostatic composition can be mixed and then loaded into said first syringe as a dry powder, or partially or fully hydrated gel. Alternatively, the additive can be provided as a separate component that is combined with diluent (such as plasma), drawn into said second syringe, and then mixed with the hemostatic composition. The additive and said hemostatic composition may be mixed as dry powders and then loaded into said first syringe. A second syringe containing diluent alone or diluent and thrombin is then connected to said first syringe and the content of these syringes are passed back and forth between said two syringes by alternating depression of their plungers. After the hemostatic composition with additive is sufficiently dispersed in the diluent, the dispersed hemostatic composition can be applied to a target site. The "target site" is the location to which the dispersed hemostatic composition is to be delivered. Usually, the target site is the tissue location of interest, but in some cases the dispersed hemostatic composition may be administered to a location near the location of interest, e.g., when the material swells in situ to cover the location of interest. The dispersed hemostatic composition can be extruded from said syringe directly through the orifice of said syringe. Alternatively, a suitable tip can be attached to said syringe and said dispersed hemostatic composition can be extruded from said syringe through the orifice of said syringe and attached tip. Tips may have a lumen and orifice that is sufficient to allow passage of said dispersed hemostatic composition, but not so large that the dispersed hemostatic composition will drip from the orifice, or so large that the extruded composition is a large, messy glob. Thus, in an aspect of the instant embodiment, the kit contains at least one tip.

The diluent in the present embodiments may also comprise, or consist entirely of, plasma, such as a patient's own plasma. In these embodiments, for example, a patient's blood is collected and prepared by standard procedures to obtain plasma. This autologous plasma is then mixed with the hemostatic composition and used in the patient as the surgeon or physician requires.

Thus, in another embodiment, there is provided composition and methods for delivering a dispersed hemostatic composition to a target site needing hemostasis. In one aspect of this embodiment, there is provided a hemostatic composition, such as a cross-linked gelatin microsphere. In this aspect, the cross-linked gelatin microspheres have a diameter from about 50 µm to about 500 µm, inclusive. In addition, the the cross-linked gelatin microspheres may further comprise pores having a pore diameter of about 20 µm. Further to this aspect, the hemostatic composition may be mixed with a wetting agent, such as poloxamer or poloxamer 188. Alternatively, the hemostatic composition may be mixed with a suspending agent, such as carboxymethylcellulose. The hemostatic composition with or without wetting agent and/or suspending agent may be formulated into a dry powder.

In a further aspect of this embodiment there is provided a hemostatic composition consisting of a cross-linked polymer and an additive selected from the group consisting of a wetting agent, a suspending agent, and both a wetting agent and a suspending agent. The cross-linked polymer may be gelatin that is either dehydrothermally cross-linked, chemically cross-linked, or cross-linked by other means, such as irradiation. The cross-linked polymer can be, for example, the cross-linked polymer is a cross-linked gelatin microsphere; a cross-linked gelatin microsphere further comprising pores having a diameter from about 50 µm to about 500 µm, inclusive, and further comprising pores having a pore diameter of about 20 µm. The hemostatic composition is prepared into a dry powder. The additive may be a wetting agent such as poloxamer 188. Alternatively, said additive is a suspending agent, e.g., carboxymethylcellulose.

Thus, the present invention also provides for a method for delivering a hemostatic composition to a site of a body of a mammal requiring hemostasis, comprising: providing a hemostatic composition as described herein; and applying said hemostatic composition to a site of a body of a mammal requiring hemostasis.

The following non-limiting examples are useful in describing the compositions and methods of the current invention.

EXAMPLES

Example 1. Materials and Methods for a Making Porous Cross-Linked Gelatin Microsphere Thermal Gelation—Liquid:

Gelatin was dissolved by heating the same in water to a concentration of 10% (w/v). Six (6) g of emulsifier (TWEEN® 80, polyoxyethylene(20)sorbitan monooleate) were added to 100 ml of the gelating solution. 500 ml of toluene containing 30 g emulsifier (SPAN® 85, sorbitane trioleate) were then stirred into the solution. The initial amount of toluene was added to act as a cavity generating compound which is dispersed as droplets within the gelatin solution. As more toluene is added, the gelatin solution becomes saturated with toluene droplets and eventually sufficient toluene is added (e.g., 500 ml) so that the gelatin solution becomes aqueous gelatin droplets dispersed in a toluene solution. When microsphere of the desired size had formed, the dispersion was cooled to a temperature beneath the solidification temperature of the gelatin. This process results in the formation of gelatin microspheres which are saturated with droplets of toluene. These toluene droplets are then removed by washing the beads with ethanol and acetone, therewith providing a gelatin microsphere which is filled with cavities. The gelatin beads are then cross-linked with glutaraldehyde, in order to further increase stability.

Thermal Gelation—Gas:

Five (5) g of emulsifier (TRITON X100™, Octoxynol-9) were added to 100 ml of gelatin solution (10% w/v). Air under high pressure was then blown through the solution, to form a large number of air bubbles therein. Gelatin microspheres were formed by dispersing the solution in 500 ml toluene/chloroform (73/27, w/v) containing 30 g emulsifier (SPAN® 85), while stirring the system. Subsequent to obtaining microspheres of the desired size, the dispersion was cooled, so as to solidify the gelatin. The organic solvents were then removed, by washing with ethanol and acetone. The gaseous cavity generating compound escapes automatically from the resultant gelatin microspheres due to their high porosity. The resultant gelatin microspheres are then be cross-linked further with, for example, glutaraldehyde.

Thermal Gelation—Solid:

Ten (10) g of calcium carbonate were added to 100 ml of gelatin solution (10% w/v), thereafter, microspheres were produced in accordance with thermal gelation—gas, above. The gelatin microspheres were treated with acid, so as to dissolve the calcium carbonate and form cavities in the beads.

Example 2. Polymerization

Acrylamid (17 g) and bisacrylamide (1.2 g) were dissolved in a Tris-buffer (100 ml, 0.05 M, pH 7). Ammonium persulphate (0.5 g/ml, 0.25 ml) and emulsifier (TRITON X-100™, 6 g) were added to the monomer solution. Then, 500 ml of toluene containing an emulsifier (SPAN® 85, 30 g) were stirred into the system. TEMED (co-catalyst, 1.3 ml) was then added to the system. The organic solvents were washed out with ethanol and acetone, upon termination of the polymerization process.

Example 3. Preparation Cross-Linked Gelatin Microspheres

Gelatin was dissolved in water at a concentration of 8% (w/v) and kept at 60° C. To 100 ml solution containing TWEEN® 80 (6% w/v, Atlas Chemie, Enschede, Netherlands) toluene containing SPAN® 85 (6% w/v, Atlas Chemie) was added continuously. The added toluene formed droplets in the gelatin solution until saturation with the droplet size depending on the mixing speed. Through addition of excess toluene to a final volume of 400 ml gelatin microspheres containing droplets of toluene were produced. After cooling the dispersion below 20° C., 200 ml ethanol was added. The formed gelatin microspheres were then further washed with ethanol and after a final wash with acetone dried and overnight at room temperature. The dry gelatin microspheres were sieved and the fraction between 125 µm and 180 µm was cross-linked with glutaraldehyde (8.8% w/v) by treating for 30 min at 15° C., after reswelling in 0.1 M phosphate buffer with pH 7.0. After removal of excess glutaraldehyde, the gelatin microspheres were heat treated at 121° C. for 20 min, which reduced the volume to about 50%, and after washing with water and acetone finally dried overnight at 60° C.

Example 4. Gelatin Microspheres and Wetting Agent

Gelatin microspheres were combined with a wetting agent to improve homogeneity of dispersion and syringeability. The gelatin microspheres can be prepared as described above, or purchased, e.g., Cultispher®-S macroporous gelatin microspheres (Percell Biolytica, Åstorp, Sweden). The wetting agent is available as a dry powder, which facilitates mixing with a dry powder microsphere. It is not necessary, however, that either of the powders is dry. In a one embodiment, the wetting agent is a poloxamer, such as poloxamer 188, NF (Spectrum Chemicals, Gardena, Calif., Cat. #P1169). Approximately 1 g to 60 g of Cultispher®-S microspheres is combined with from 1 g to 3 g of poloxamer 188, and the dry powders are mixed together until a homogenous mixture is achieved. Mixing can take place using a variety of techniques and equipment known in the art. Alternatively, the wetting agent is a component of the diluent used to disperse the gelatin microspheres. In this embodiment the wetting agent is present in the diluent at about 0.25% w/v to 5% w/v. For each 1 mL of diluent with wetting agent, approximately 125 mg to 175 mg of Cultispher®-S microspheres is added and then the cross-linked gelatin microspheres and the diluent with wetting agent are admixed, for example by passing back and forth between two interconnected syringes, until the microspheres are mixed to a paste-like consistency.

Example 5. Microsphere and Suspending Agent for Dispersion and Syringeability

Gelatin microspheres were combined with a suspending agent to improve homogeneity of dispersion and syringeability. The gelatin microspheres can be prepared as described above. In one embodiment, the gelatin microspheres were Cultispher®-S microspheres (Percell Biolytica). The suspending agent is available as a dry powder, which facilitates mixing with a dry powder microsphere. It is not necessary, however, that either of the powders are dry. In one embodiment the suspending agent is a carboxymethylcellulose, such as a medium-viscosity carboxymethylcellulose (Spectrum, Cat. #CA192). The gelatin microsphere and the suspending agent powder are mixed together until a homogenous mixture is achieved. Mixing can take place using a variety of techniques and equipment known in the art. Alternatively, the suspending agent is a component of the diluent used to disperse the gelatin microspheres. In this embodiment the suspending agent is present in the diluent at approximately 0.25% w/v to 5% w/v. For each 1 mL of diluent with suspending agent, approximately 125 mg to 175 mg of Cultispher-S microspheres are added and then the cross-linked gelatin microspheres and the diluent with suspending agent are admixed, for example by passing back and forth between two interconnected syringes, until the microspheres are mixed to a paste-like consistency.

Example 6. Microspheres and Wetting Agent for Dispersion and Syringeability

Gelatin microspheres can be combined with a wetting agent and a suspending agent to improve homogeneity of dispersion and syringeability. The gelatin microspheres can be prepared as described above. In a one embodiment, the gelatin microspheres are Cultispher®-S microspheres (Percell Biolytica). Both the suspending agent, which is carboxymethylcellulose, and the wetting agent, which is poloxamer 188, are dry powders. The gelatin microspheres are then mixed with a powder combination of equal parts suspending agent and wetting agent until a homogenous mixture is achieved. Alternatively, both the suspending agent and the wetting agent are components of the diluent used to disperse the gelatin microspheres. In this embodiment, the gelatin microspheres and the diluent with suspending/wetting agent are admixed, for example by passing back and forth between two interconnected syringes, until the microspheres are mixed to a paste-like consistency.

Example 7. Flowable Hemostatic Matrix

A flowable hemostatic matrix was prepared consisting of a syringe containing the matrix coupled to another syringe containing diluent (saline, saline containing thrombin, or comparable vehicle). The matrix consisted of cross-linked gelatin powder (Cultispher®-S macroporous gelatin microspheres) with or without additives such poloxamer 188 or carboxymethyl cellulose. The hemostatic matrix, with or without additives, was weighed and transferred into the syringe. Typically, the compositions included 675 mg of Cultispher®-S microspheres with or without additives ranging from 60:1 w/w to 3:1 w/w ratio (microsphere:additive). The components were placed in a capped syringe barrel (with plunger removed) and the plunger was replaced behind the powder. A separate syringe containing 4.5 mL of diluent was joined to the powder syringe, using a female-to-female luer connector. The dry powder and buffer were then mixed using twenty passages. The hemostatic matrix was allowed to hydrate for 60 sec, and the matrix was then dispensed. Dispensed preparations only containing the Cultispher®-S microspheres (without additive) exhibited non-uniformity regarding the aqueous content; that is, initial aliquots were more "wet" than the subsequent aliquots. This phenomena was termed "sponging-out". Including wetting agents (e.g., poloxamer 188) or suspending agents (carboxymethylcellulose) as additives minimized this phenomenon, however. It was also observed and quantitatively determined using a syringe force meter that the force required to extrude the matrices containing additives was more consistent and was minimized when dispensing the entire contents of the syringe. It was not practical to dispense matrices of Cultispher®-S microspheres without additives through narrow-bore administration tips that were affixed to the syringe prior to dispensing. Including wetting agents (i.e., poloxamer 188) or suspending agents (carboxymethylcellulose) as additives minimized this phenomenon, however, allowing the entire contents of the syringe to be dispensed with minimal force through narrow-bore administration tips.

Example 8. In Vivo Efficacy Comparison Between Non-Irradiated CultiSpher®-S Microcarrier Beads and Solid Beads Utilizing the Rat Heminephrectomy Bleed Model A study was designed to compare hemostatic efficacy between porous, cross-linked gelatin microspheres and non-porous (solid), cross-linked gelatin microspheres. Microspheres were prepared as above, with the exception that a single dose of 150 mg/mL thrombin was included for both microsphere preparations (placebo is porous Cultispher®-S microspheres without thrombin).

The Mean Time to Hemostasis comparison of animals treated with the porous, cross-linked gelatin microspheres and thrombin revealed a greater reduction in TTH in animals treated versus the solid microspheres or placebo. Specifically, mean TTH was as follows (mean±sd) about 112±15 sec for placebo, approximately 79±37 sec for the solid microsphere and about 45±6 sec for porous microsphere. Without being limited to any particular theory, the enhanced reduction in TTH shown by porous, cross-linked gelatin microsphere group maybe explained by the porosity of the microsphere, wherein said pore creates a greater surface area allowing platelets to enter and mix thus creating a more rapid time to clotting.

Another advantage of porous, cross-linked gelatin microspheres compared to the solid beads was the consistency of the matrix. The porous, cross-linked gelatin microsphere matrix was easy to dispense and easy to apply onto the cut kidney surface from the first minute of reconstitution until 90 min. In comparison, the solid bead matrix at 1 min post-reconstitution ran off the kidney surface, and at 60 min became very crystalline-like and difficult to apply to the kidney surface.

Example 9. TEG Assays

Thromboelastography (TEG) assays were performed according to published assays. See Roche et al., 96 Anesth. Analg 58-61 (2003). A stock thrombin solution consisted of a 5000 Unit vial of recombinant thrombin (e.g., RECOTHROM®, ZymoGenetics, Inc., Seattle Wash.) dissolved in 0.5 mL of 0.9% saline for a final volume of 600 µl and a concentration of 8333 IU/mL. Dilutions were made of the stock in Saline plus 0.1% BSA so that 10 µl aliquots yield a final concentration in the TEG assay between 25 IU and 200 IU per ml. The 10 µl of thrombin was added to dry microsphere powder, producing a swollen gel. This allowed a more homogenous mixing of the thrombin and blood prior to clot initiation. Assays were performed with two TEG 5000s and monitored using commercial software such as TAS 4.2.3 (HAEMOSCOPE™ Corp., Niles, Ill.).

Blood samples were obtained from rabbits prior to and after treatment with clopidogrel bisulfate. Each animal received three, daily 20 mg/kg oral doses of clopidogrel bisulfate. A 75 mg clopidogrel bisulfate tablet was crushed and suspended in 3 mL of sterile distilled water. The rabbits received between 1.6 to 2.2 mL of the suspension by gavage. Blood samples were taken after the third daily treatment. According to TEG protocols, on Day 1 of the AV shunt model, the rabbit blood is named "Rabbit Mo/Day". This name is the same for each subsequent collection of the same rabbit's blood through out the three-day experiment. For example, on Day 1 pretreatment blood and blood 2 hr after the clopidogrel bisulfate gavage is received on November 12 and named "Rb 11/12." On Day 2, 11/13 and Day 3, 11/14 the sample remains Rb 11/12. Blood was collected in citrate unless specified. Blood was re-calcified in the TEG assay cup with 20 µl of 0.2M $CaCl_2$, 0.9% NaCl, pH 7.4 (stock $CaCl_2$) as described in the HAEMOSCOPE™ TEG protocol.

Figure 1B:
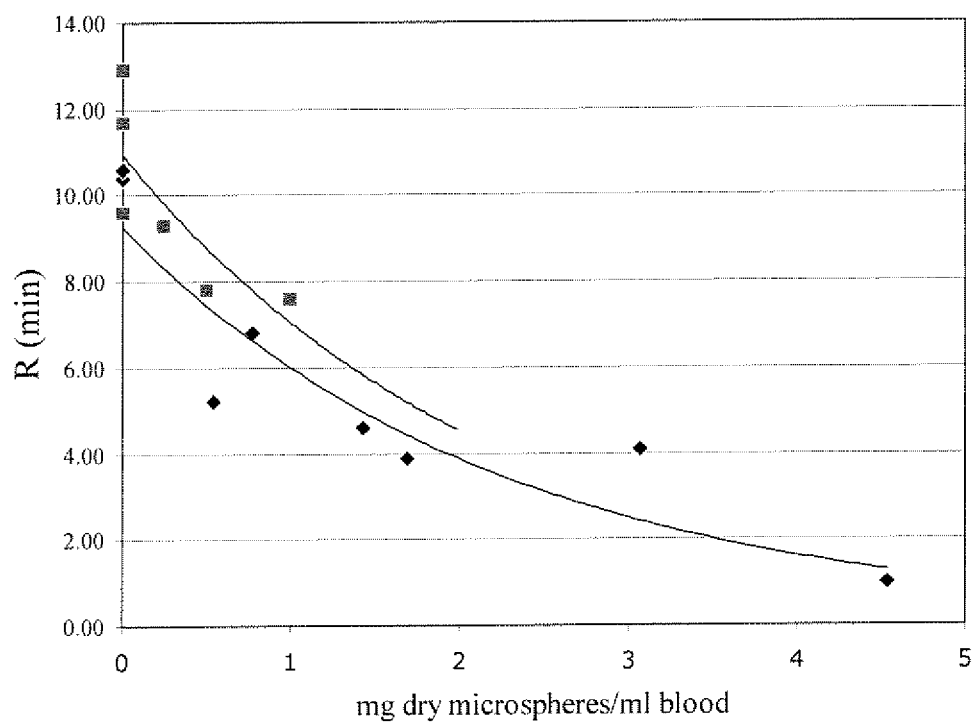

The data in FIG. 1 was generated using protocol 2 for microsphere gel-only and protocol 3 for microsphere gel and thrombin. The assays in FIGS. 2, 3, and 4 were performed using protocol 5 with normal citrated blood with or without heparin. Heparin was added as described in protocol 4.

Protocol 1. Minus-Heparin Assay:

Prior to the addition of heparin, the blood was recalcified to determine the pre-heparin TEG parameters. The results of the heparin free assays are similar to for both the pretreatment and clopidogrel bisulfate treated blood samples. Some of the clopidogrel bisulfate blood samples have an early R value suggesting that they are hyper-coagulable. These results are consistent with those reported in the art.

Protocol 2. Minus-Heparin Assays with Microsphere Gel Present:

The mixing of microsphere gel may be modified while developing the particular method. For example, one microsphere gel preparation was made by allowing gel to swell fully, and then adjusted to a 1:1 suspension in 0.9% NaCl. The gel was pipetted into the TEG cup just prior to the assay.

Protocol 3. Thrombin Plus Microsphere Gel:

Dry microsphere powder (23.5 g) was mixed with 4.7 mL of 5000 IU/mL recombinant thrombin and 56.9 mL of 0.9% Saline. This resulted in a hydrated gel with 1 IU thrombin per mg dry microsphere powder. The same gel to saline ratio (1:2.6) was used as a minus thrombin control. Various amounts of the hydrated gel was weighed into a TEG assay cup using a spatula just prior to the assay.

Protocol 4. TEG Assays with Heparin:

Heparin was added to the blood (1 IU heparin/mL blood) in order to determine the effect of heparin alone and heparin plus clopidogrel bisulfate on the reaction time (R), reaction rate (K) and maximum amplitude (MA) for all three days of clopidogrel bisulfate treatment. The last blood sample on Day 3 is assayed with heparin transfused into the rabbit (heparin 'on board') just prior to the start of the AV shunt model. The transfused heparin is approximately 1 unit/mL blood. This level of heparin is just sufficient to obtain a APTT of >400 seconds.

Protocol 5. Thrombin Activation of Heparinized Blood:

Prior to the assay, a suspension of either 50 mg or 100 mg of microsphere gelatin beads in 1.5 mL of distilled USP irrigation water was allowed to swell for 15 min by rocking. Then, 35 µl of the gelatin bead suspension was dispensed into each assay cup and allowed to dry at 37° C. for 30 min. The dry gel is either 1.21 mg or 2.42 mg per cup respectively.

The TEG assay is composed of 330 µl Blood, 20 µl stock $CaCl_2$ solution, 10 µl thrombin ranging in concentration between 25 U and 8333 U in microsphere gel for a total volume of 360 µl.

When high thrombin is added directly into blood by standard pipetting techniques the fibrinogen is converted to fibrin faster than mixing can occur. This results in a non-homogenous clot. Observational data confirms this: (a) the TEG maximum amplitude (MA) may collapse and stabilize at a lower value; and (b) the pipette tip may suck in part of the clot during mixing.

In order to overcome problems mixing, microsphere gel was added to the TEG assay cup. The swelling of the microsphere gel occurs completely during the first minute. FIG. 4A shows the reaction rate of the clot (R). R is the minutes from the start of the assay to the first measurable clot strength (2 mm amplitude). When the thrombin is added to dry microsphere gel, the R is increased indicating that the clot kinetics is slower than when thrombin is added directly. The prediction that thrombin entrapment within microsphere pores would allow better mixing was also supported by the maximum clot strength MA (FIG. 4B). MA is related to G by the formula: G=5000 MA/(100−MA). Without the microsphere gel, the MA actually declined with increasing thrombin, whereas the thrombin plus microspheres gel maintained strength. The diffusion rate of thrombin from the gel was inferred to be slower because the reaction rate was slower.

The microsphere gel served as a pro-coagulant as well as a matrix for the delivery and mixing of thrombin. This is may be due to the activation of the Contact Pathway by cross-linked gelatin. The cross-linked gelatin may also activate platelets via receptors such as GP VI, the collagen receptor.

Clot formation in the presence of heparin first requires the saturation of Anti-thrombin (primarily AT III). Once anti-thrombin is overcome, fibrin formation and platelet activation via the thrombin receptors can occur. Thrombin activation of platelets also bypasses platelet activation inhibitors such as clopidogrel bisulfate and aspirin. One would predict that such thrombin activation would not bypass platelet aggregation inhibitors INTEGRILIN® (eptifibatide, Schering-Plough, Kenilworth, N.J.), REOPRO® (Abciximab, Centocor B.V., Leiden, Netherlands), and AGGRESTAT® (tirofiban, Merck & Co, Inc, Whitehouse Station, N.J.).

Example 10. Clotting in the Presence of Microsphere/Thrombin Formulations

Blood was collected in citrate and calcium (11 mM) was added back to initiate the assay. Under these conditions there is sufficient thrombin generated from prothrombin in the blood to form a strong clot. Without coagulation inhibitors in the blood ('on board') the primary advantage in adding thrombin to stanch bleeding is to decrease the clotting time from 12-21 min to less than 1 min. This can be accomplished with about 3 IU thrombin/mL of blood (FIG. 1, microspheres and thrombin).

Microsphere gel was also found to strengthen clots. The uninhibited coagulation system in normal blood generates a strong clot without added thrombin. Clot strength may be increase, however, by adding increasing amounts of microsphere gel to the blood. Clots formed with microsphere gel and thrombin exhibit a >40% increase in strength (FIG. 1). These clots were formed with relatively low thrombin concentrations ≤3 IU/mL.

Figure 2:
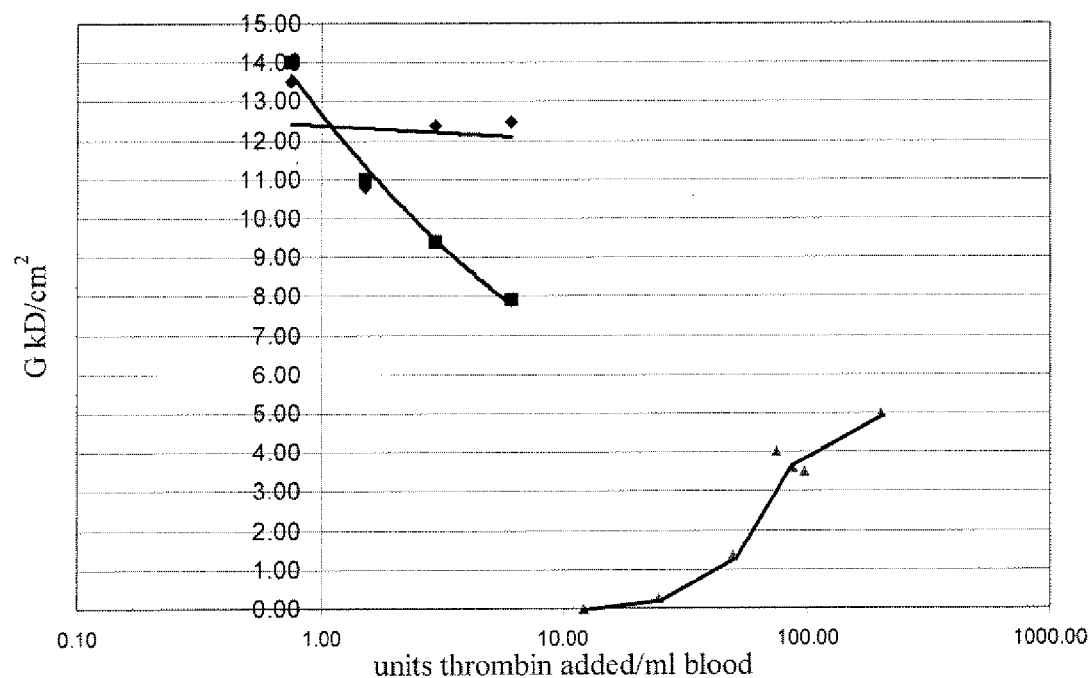
FIG. 2 shows that high levels of thrombin are required to overcome heparin. A partial clot often forms in the mixing pipette when high thrombin is introduced into blood. Polymer microspheres improves the mixing of thrombin with blood and improves clot formation. To partially overcome heparin inhibition, 75 IU to 100 IU thrombin/mL is required. The formulation of microspheres and thrombin also form a more homogeneous clot. The blood was re-calcified with 10 mM $CaCl_2$, with or without 3.4 mg microspheres/ml gel; ♦ thrombin mixed with microsphere gel; ■ thrombin mixed directly; ▲ thrombin and microsphere gel mixed with 1 IU/mL heparin.
Figure 3:
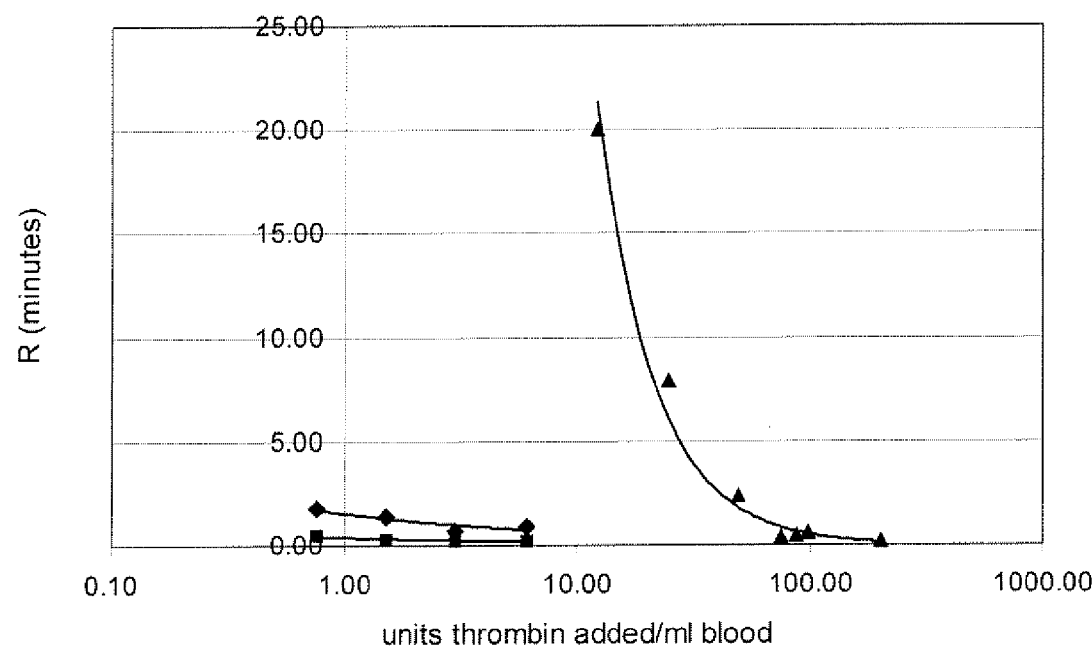
FIG. 3 shows that high levels of thrombin are required to overcome the effects of heparin. A partial clot often forms in the mixing pipette when thrombin is introduced into blood. Thrombin in microspheres gel improves the homogenous mixing of thrombin with blood and improves clot formation. In the presence of 1 IU/mL heparin, almost 100-times more thrombin is required for the same reaction time without heparin. The formulation of thrombin in microsphere gel reduces clot initiation time (R) by slowing the release of thrombin. Blood was re-calcified with 10 mM $CaCl_2$ with or without microsphere gel, and with or without heparin. ♦ thrombin mixed with 1.2 mg gelatin beads; ■ thrombin added directly to blood; ▲ microsphere gel, thrombin, and 1 IU heparin.

High thrombin concentration plus microsphere gel is advantageous when coagulation inhibitors are present in the blood. Under these conditions very large amounts of thrombin are typically required to overcome clotting inhibition. As shown in FIG. 2 (strength) and FIG. 3 (reaction time), in which clots assayed with normal citrated blood and clots of blood inhibited with 1 IU/mL heparin are superimposed. There is a 100-fold increase in the thrombin concentration required to overcome heparin inhibition. The actual concentration of thrombin in the microsphere gel (93 µl gel, fully swollen, per ml blood) is about ten-times greater than the amount in the blood. The thrombin concentration required in the gel to form a clot is therefore approximately 750 IU to 2000 IU thrombin/mL gel. This clot does not obtain the strength of the heparin-free blood, but is within the range of clot strength considered normal for human blood (Roche et al., 96 Anesth. Analg 58-61 (2003)). The addition of clopidogrel bisulfate to heparin increases the requirement for thrombin even more (FIG. 6). Clopidogrel bisulfate inhibition is usually detected by platelet mapping but this data suggests that it may also be measured in the presence of heparin when exogenous thrombin is added.

Example 11. In Vivo Testing of Hemostatic Compositions Comprising Thrombin

A rabbit vascular anastomotic bleeding model was employed. PTFE arterial venous grafts were punctured four times with a 4-0 suture needle, immediately wrapped with absorbable gelatin sponge, USP, soaked with placebo (vehicle) or rThrombin (1000 IU/mL or 125 IU/mL). Overall mean TTH was calculated for animals treated with placebo, standardized doses of heparin alone or heparin with clopidogrel bisulfate. Results were analyzed using linear models with robust standard error estimates.

rThrombin at a concentration of 1000 IU/mL completely reversed the effects of heparin or heparin with clopidogrel bisulfate on TTH, whereas rThrombin 125 IU/mL did not. rThrombin 1000 IU/mL resulted in a significantly lower mean TTH compared to 125 IU/mL ($p<0.0001$) in both heparin or heparin with clopidogrel bisulfate-treated animals, and both concentrations of rThrombin were superior to their respective placebo controls ($p<0.001$).

Potent platelet inhibition is commonly encountered in vascular and general surgery; over 18 million prescriptions for clopidogrel bisulfate are written annually in the U.S. In this in vivo study, rThrombin 1000 IU/mL resulted in a significantly lower mean TTH than 125 IU/mL and completely reversed the effects of heparin or heparin with clopidogrel bisulfate. These results support the broad clinical utility of topical rThrombin at 1000 IU/mL as the standard of care.

Similarly, when such different thrombin concentrations are applied in the context of the hemostatic microspheres of the present invention, a similar effect is expected; that higher thrombin concentrations of 1000 IU/mL or more have a lower mean TTH. Moreover, the in vivo data supports the potential application of higher thrombin concentrations in the hemostatic microspheres in applications where such higher concentrations are desirable.

Example 12. In Vivo Testing of Hemostatic Compositions Comprising Thrombin

In Vivo Study Design: The various treatment groups are shown in Table 1 for different rThrombin concentrations, and Table 2 for animals pretreated with clopidogrel bisulfate.

For each set of experiments, control parameters were used to demonstrate consistency among animals and standardization between grafts include: body weight, body temperature baseline/terminal for each graft, baseline/terminal mean arterial pressure (MAP) for each graft, baseline/terminal AV shunt blood flow rate for each graft, and baseline and post heparin treatment activated partial thromboplastin time (APTT).

TABLE 1

Study Design with Varying Concentrations of rThrombin

| Treatment Groups | Units of rThrombin (IU/mL) | No. Grafts/Group |
|---|---|---|
| AGS + Placebo | 0 | 12 |
| AGS + rThrombin | 31.25 | 8 |
| AGS + rThrombin | 62.5 | 8 |
| AGS + rThrombin | 125 | 8 |
| AGS + rThrombin | 1000 | 8 |

AGS = absorbable gelatin sponge, USP,
TTH = Time to hemostasis

TABLE 2

Study Design with 125 IU/mL or 1000 IU/mL in Rabbits
Pretreated with clopidogrel bisulfate and Heparin

| Treatment Groups[a] | Anticoagulant | No. Grafts/Group |
|---|---|---|
| AGS + Placebo | clopidogrel bisulfate/heparin | 10 |
| AGS + rThrombin 125 IU/mL | clopidogrel bisulfate/heparin | 14 |
| AGS + rThrombin 1000 IU/mL | clopidogrel bisulfate/heparin | 14 |

AGS = absorbable gelatin sponge, USP,
TTH = Time to hemostasis
[a]Data not shown-rabbits treated with clopidogrel bisulfate alone but no heparin for control purposes Animals:

Approximately 12-week-old female New Zealand White rabbits, weighing 2.0 kg to 3.8 kg, Lot No. 2525 (Charles River Laboratories, Hollister Calif.) were used for this study. Animals were acclimated to the facility for 7 days to 10 days before the experiment, and were maintained in good condition at the ZymoGenetics Vivarium. The study protocol was approved by the Institutional Animal Care and Use Committee.

Absorbable Gelatin Sponge and Test Articles:

A gelatin sponge (GELFOAM® absorbable gelatin compressed sponge, USP, Pharmacia & Upjohn Co., Kalamazoo, Mich., size 100) was cut into 2×4×1 cm strips and combined with test article (rThrombin or placebo).

Recombinant human thrombin, rThrombin, (RECOTHROM®, ZymoGenetics, Inc., Seattle, Wash.) material consisted of a 5,000 IU/vial of lyophilized product manufactured by Abbott Laboratories. On the day of the study, a vial of rThrombin was removed from the refrigerator, and allowed to sit at room temperature for a minimum of 20 to 30 min before being reconstituted in 5 mL of sterile saline yielding a 1000 IU/mL solution. The 1000 IU/mL solution was further diluted with vehicle to yield 31.25, 62.5, and 125 IU/mL solution. Vehicle solution consisted of the formulation for rThrombin without active ingredient: 1.6 mM Histidine. 200 mM NaCl, 1.28 mM $CaCl_2$, 0.96% w/v sucrose, 1.28% w/v mannitol, 0.032% PEG-3350, and pH adjusted to 6.0.

Clopidogrel Bisulfate Administration:

Each animal received three daily 20 mg/kg oral doses of clopidogrel bisulfate prior to undergoing AV shunt. A 75 mg clopidogrel bisulfate tablet was dissolved in 3 mL of sterile water yielding a working concentration of 25 mg/mL. Each animal received between 1.6 2.2 mL of the 25 mg/mL solution per day by gavage.

Rabbit AV Shunt Procedure:

Each rabbit was weighed and immobilized with Ketamine hydrochloride (50 mg/kg) via intramuscular injection. The animal was placed on the surgical table in a nose cone connected to a precision gas anesthesia vaporizer, which delivered anesthesia (IsoFLO® isoflurane, USP, Abbott Labs., North Chicago, Ill.) vapor concentration of 4% to 5% for induction, and 1% to 2% for maintenance of a surgical plane of anesthesia, with a flow rate of 1% to 2% L/min $O_2$. The animal was placed on a water-jacketed heating pad maintained at 37° C. during the experimental period, and a rectal thermoprobe was inserted for monitoring of body temperature. Blood pressure, mean arterial pressure, and body temperature were measured throughout the experiment.

To create the AV shunt, a skin incision was made on ventral surface of the neck. The right external jugular vein and left common carotid artery were isolated and cannulated with 3 to 4 cm length Micro-Renathane tubing (MRE 080, 0.080 O.D."×040 I.D.", Braintree Scientific, Braintree, Mass.) which was connected to a 15 cm length of silicone catheter tubing (7-French, 0.078 LD"×0.125 O.D.", Access Techs., Skokie, Ill.). The catheters were exteriorized and connected with a 3 mm diameter, 2 cm to 2.5 cm long polytetrafluoroethylene (PTFE) graft segment (Bard Peripheral Vascular Inc., SN AFEP 7108) producing an arterial-venous shunt linking the blood flow of the left carotid artery and the right jugular vein. Blood flow through the shunt was measured using a Transonic System Inc. Flowmeter model TS410 (Ithaca, N.Y.).

Each rabbit received 100 U/kg intravenous (i.v.) bolus injection of heparin followed by a continuous 50 U/kg/mL infusion of heparin (porcine derived, Abraxis Pharma. Prods., Schaumburg, Ill.) at a flow rate of 5 mL/hr via the femoral vein. Prior to heparin treatment and approximately 5 min to 10 min post i.v. heparin bolus treatment APTT was measured. In order to assure that the animal was anticoagulated (APTT >400 seconds) the animal received a 50 U/kg i.v. bolus injection of heparin every third graft.

Suture Hole Bleed and Measurement of TTH:

Prior to creating suture holes in any of the grafts, a baseline MAP of approximately 55 mm Hg had to be achieved and an APTT value greater than 400 sec. Assessment of suture hole bleeding consisted of puncturing the center section of the PTFE graft segment with a 2 4-0 18 inch silk suture needle (reverse cutting needle size P-3, Ethicon Inc., Somerville, N.J.) creating four needle holes.

Immediately following suture hole punctures the absorbable gelatin sponge (AGS) containing test article was wrapped around the graft completely covering the suture holes. The AGS containing test article was immediately covered with gauze sponges and continuous digital pressure applied for 60 sec of the 5-min study period. At the end of the 60-sec period, the gauze sponges were visually inspected for bleeding. If cessation of bleeding did not occur, the gauze sponges were replaced with new gauze sponges, test article was reapplied followed by digital pressure. This process was repeated until no visible blood was observed on the gauze sponges. Time to hemostasis was recorded in seconds. In the event TTH was not achieved within 300 sec the study was terminated and 300 sec was recorded. At the conclusion of the 5-min study period, the clot at suture hole sites was assessed is some of the grafts. Following assessment of clot burst the catheters were clamped flushed with saline, the polytetrafluoroethylene (PTFE) segment was removed and fresh PTFE segment was inserted. Once blood pressure achieved a reading of 55 mm Hg the process was repeated. In the event 55 mm Hg MAP could not be achieved, the animal was euthanized.

Suture Hole Clot Burst Assessment:

In some of the heparin-only treated rabbits, and in all of the clopidogrel bisulfate/heparin treated rabbits, clot burst at the suture hole sites was assessed at the end of the 5 min experimental, provided TTH was achieved. The procedure involved clamping off blood flow to the jugular vein catheter approximately 2 cm to 3 cm downstream from the graft for a period of 10 sec. Complete obstruction of blood flow created an increase in blood pressure from the arterial flow. In the event blood seeped through the AGS during the 10-sec-period then clot burst was recorded as being positive. IF no leakage was observed the clot burst was recorded as being negative.

Statistical Analysis of TTH:

The linear model for time to hemostasis is given by where Y is TTH in seconds. X is rThrombin dose group as a categorical variable, Z is the clopidogrel bisulfate treatment coded as "0" for no clopidogrel bisulfate and "1" for with clopidogrel bisulfate, and is the interaction between rThrombin dose group and clopidogrel bisulfate treatment.

Results:

The primary efficacy endpoint for this study was time to hemostasis (TTH). The TTH values ranged from 65 sec to 300 sec, and mean TTH was calculated for each treatment group (Table 3, below). Comparison of the four concentrations of rThrombin versus vehicle/control demonstrated a concentration dependent reduction in TTH. A significant reduction in TTH ($p<0.001$) was observed between grafts treated with 62.5 IU/mL, 125 IU/ml and 1000 IU/mL rThrombin+AGS (142±35.7, 87±22.5, 71±4.6) as compared to placebo plus AGS (249±67.1) and 31.25 IU/mL rThrombin plus AGS (213±39.3).

TABLE 3

Group Mean ± SE TTH for Each Group, Following Treatment with rThrombin at Increasing Doses

| Treatment Groups | rThrombin Dose IU/mL | Number of Grafts/Group | TTH ± SE (s) |
| --- | --- | --- | --- |
| AGS + Vehicle | 0 | 12 | 249 ± 67.1 |
| AGS + rThrombin | 31.25 | 8 | 213 ± 39.3 |
| AGS + rThrombin | 62.5 | 8 | 142 ± 35.7 |
| AGS + rThrombin | 125 | 8 | 87 ± 22.5 |
| AGS + rThrombin | 1000 | 8 | 71 ± 4.6 |

AGS = absorbable gelatin sponge, USP

Even in the presence of a systemic anti-coagulant like clopidogrel bisulfate, rThrombin significantly reduced the TTH in the rabbit AV shunt model (Table 4). A significant reduction in TTH was observed in grafts treated rThrombin (both 125 IU/mL and 1000 IU/mL) plus AGS, as compared to vehicle plus AGS ($p<0.001$). The reduction in mean TTH observed in grafts treated with 1000 IU/mL rThrombin was significantly greater, however, as compared to the 125 IU/mL rThrombin group ($p<0.0001$). It should also be noted that the variability of the TTH measurement was much less with in grafts treated with the higher concentration of rThrombin. Thus, the concentration of rThrombin at the wound site had a highly significant effect on TTH in the model in the presence of the anticoagulant clopidogrel bisulfate.

TABLE 4

Group mean ± SE TTH for Each Group, Following clopidogrel bisulfate Treatment with or without rThrombin

| Treatment Groups | Anticoagulant | Number of Grafts/Group | TTH ± SE(s) |
| --- | --- | --- | --- |
| AGS + Placebo | clopidogrel bisulfate/ Heparin | 10 | 270 ± 32.5 |
| AGS + rThrombin 125 IU/mL | clopidogrel bisulfate/ Heparin | 14 | 183 ± 62.2 |
| AGS + rThrombin 1000 IU/mL | clopidogrel bisulfate/ Heparin | 14 | 73 ± 8.4 |

AGS = absorbable gelatin sponge, USP

Model control parameters included: body weight, body temperature baseline/terminal for each graft, baseline/terminal mean arterial pressure (MAP) for each graft, baseline/terminal AV shunt blood flow rate for each graft, and baseline post heparin treatment activated partial thromboplastin time (APTT). Individual animal body weight, starting and ending study APTT were similar between groups. Comparison of baseline APTT and terminal APTT showed a 2.6-fold or greater increase values in terminal APTT, which was expected due to heparin administration. Group mean comparison of body temperature, MAP, blood flow and amount of test article applied to each gelfoam were similar for each group.

Figure 5:
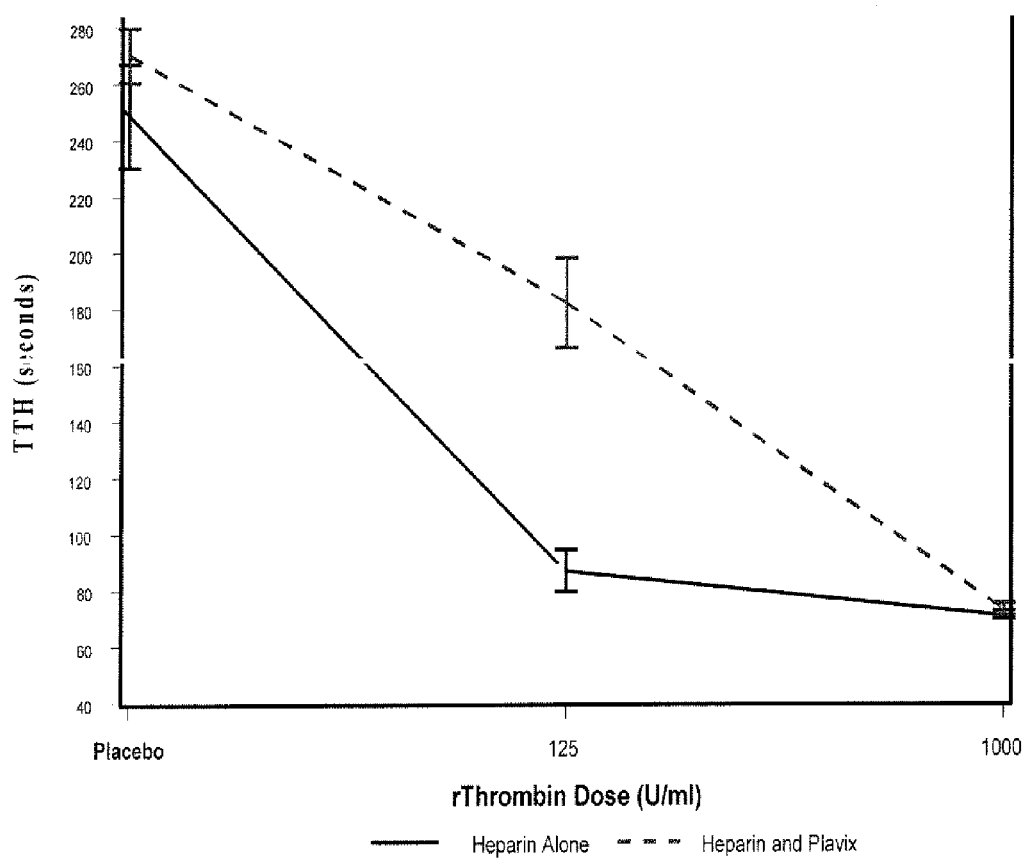
FIG. 5 is a graph presenting model estimates of time to topical hemostasis (TTH) (mean SE) versus recombinant thrombin (rThrombin) dose.

In FIG. 5, analysis of the mean TTH demonstrates significant reduction in TTH in grafts treated with either dose rThrombin as compared to its respective placebo control ($p<0.001$). Also, a significant reduction in group mean TTH was observed in grafts treated with 1,000 IU/mL rThrombin as compared to the 125 IU/mL rThrombin group ($p<0.0001$). A secondary endpoint of interest was an evaluation of the strength of clots formed under the various conditions of rThrombin concentration and anticoagulation. Clot burst at the suture hole sites was assessed at the end of the 5 min experimental, provided TTH was achieved. No significant differences in incidence of clot rupture were observed between the different rThrombin concentrations tested in rabbits anti-coagulated with heparin alone. In the clopidogrel bisulfate treated rabbits, there was a much higher incidence of clot rupture, however, in grafts treated with 125 IU/mL of rThrombin (79%), as compared with 0% of the grafts treated with 1,000 IU/mL of rThrombin (FIG. 6).

The photos show the rabbit AV shunt model grafts used in clot burst assessment with either 125 IU/mL rThrombin (top three photos), or 1,000 IU/mL rThrombin. It was observed that 79% grafts treated with 125 IU/mL tested positive for clot burst at the suture hole site as compared to 0% of the grafts treated with 1,000 IU/mL of rThrombin.

Similarly, when such different thrombin concentrations are applied in the context of the hemostatic microspheres of the present invention, a similar effect is expected; that higher thrombin concentrations of 1,000 IU/mL or more have a lower mean TTH. Moreover, the in vivo data supports the potential application of higher thrombin concentrations in the hemostatic microspheres in applications where such higher concentrations are desirable.

Example 13. In Vitro Study

TEG Assay Preparation; Samples from Rabbit AV Model:

Blood was collected 2 hr post-clopidogrel bisulfate treatment as detailed in the AV shunt model methods. The blood was collected in citrate and re-calcified in 20 μl of 0.2 M $CaCl_2$, 0.9% NaCl, pH 7.4, just prior to the assay according to the TEG assay protocol. One unit/ml heparin was added to in vitro to samples from rabbits during pre-clopidogrel bisulfate treatment and for Day 1 samples. The samples from the rabbits after Day 3 clopidogrel bisulfate treatment included heparin that was transfused into rabbits such that the heparin is approximately 1 U/mL of blood (animals had an APTT of >400 seconds).

Adaptations to TEG Method to Allow Analysis of Exogenous rThrombin Addition:

The citrated rabbit blood was recalcified according to the standard TEG protocol. See Roche et al., 96 Anesth. Analg 58-61 (2003). The blood clotted within normal parameters for rabbit blood without exogenous thrombin. Direct addition of 0.76 to 6.1 IU/mL rThrombin initiates clot formation at a rate that precludes TEG measurement. A modified method of thrombin addition Haemoscope covering a tenfold range in the amount of thrombin was used for clot initiation.

Thromboelastograph Study Design:

TEG measures time latency for initiation of the clot, time to initiation of a fixed clot firmness of 20-mm amplitude, kinetics of clot development as measured by the angle (α) maximum amplitude (MA) of the clot R value (reaction time) is measured from the beginning of the tracing to the point where the curve is 1 mm wide Clot strength (shear elastic modulus) is defined as G (dynes/cm$^2$).

Results:

The in vivo rabbit experiments (Example 11 and Example 12) indicated that increasing doses of rThrombin could decrease TTH in the AV shunt model. FIG. 6 plots clot strength G (Dynes/cm$^2$) for clots from rabbits prepared for the AV shunt model. Blood was collected from rabbits two hours after administration of clopidogrel bisulfate. The blood was collected in citrate recalcified, and used in the TEG assay. Samples from pretreatment and Day 1 elopidogrel bisulfate treated rabbits were incubated with 1 U/mL heparin in vitro, and heparin added during the AV shunt procedure for the Day 3 clopidogrel bisulfate sample.

Figure 6A:
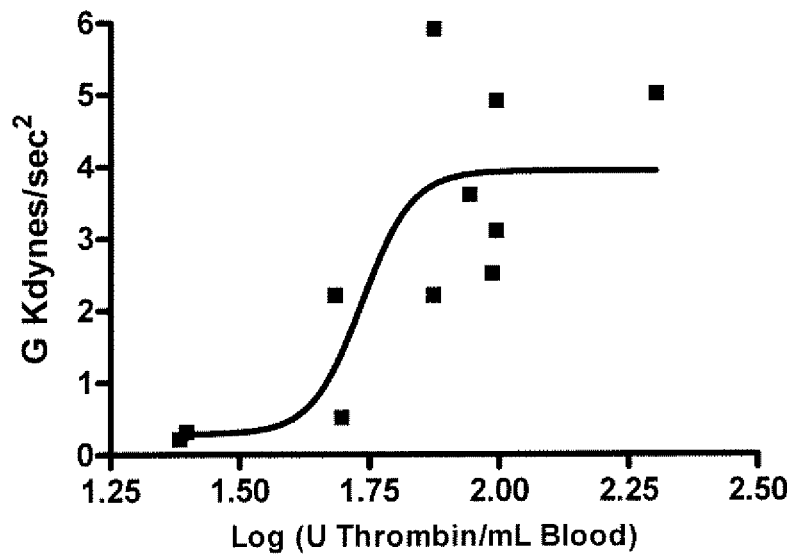
FIGS. 6A and 6B show the Effect of rThrombin Concentration on Maximum Clot Strength ($G_{max}$) on Heparinized Rabbit Blood pre and post Treatment with Clopidogrel. Blood samples were collected from three rabbits prior to Clopidogrel treatment and 1 IU/mL Heparin was added (top, 6A). Blood samples were taken again after Clopidogrel treatment and in vivo heparinization (bottom, 6B). Each point represents the peak strength $G_{max}$ of a single TEG assay at one thrombin concentration. Thrombin concentrations ranged from 25 IU to 200 IU per mL of blood. Fitting the data to log a Dose equation demonstrates that higher thrombin concentrations are required to overcome heparin (EC50=54 IU/mL) and heparin plus clopidogrel (EC50=66 IU/mL).
Figure 6B:
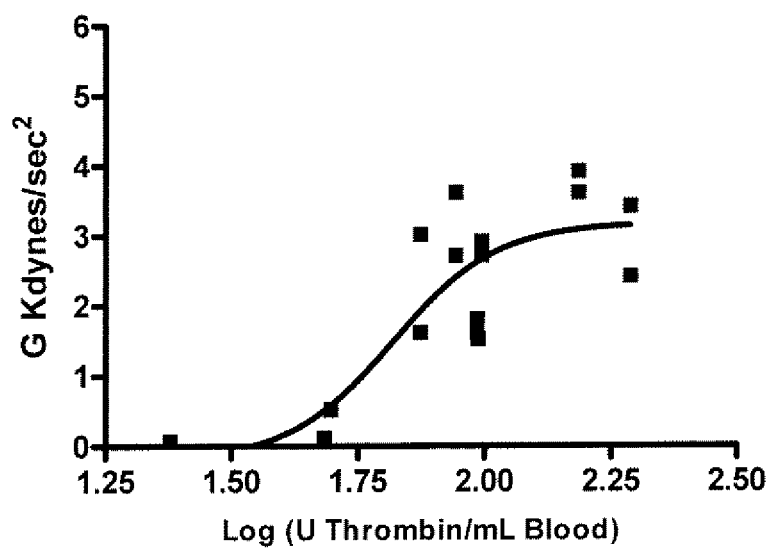

In experiments conducted in rabbits not pretreated with clopidogrel bisulfate, increasing the concentration of rThrombin used in vitro increased the clot strength (shear elastic modulus) as defined as G (dynes/cm$^2$), shown on the Y-axis in FIG. 6A, and demonstrated an EC50 of 54 U/ml. In further experiments, clot strength for samples from rabbits pretreated with clopidogrel bisulfate for 2 hr can be seen in FIG. 3B, with an EC50 of 66 U/mL. In both cases, the strength of clot increased with increasing rThrombin concentrations, supporting the conclusions from the in vivo AV shunt model.

Similarly, when such different thrombin concentrations are applied in the context of the hemostatic microspheres of the present invention, a similar effect is expected; that higher thrombin concentrations of 1,000 IU/mL or more have a lower mean TTH. Moreover, the in vitro data supports the potential application of higher thrombin concentrations in the hemostatic microspheres in applications where such higher concentrations are desirable.

Example 14. Confirmation of Hemostatic Activity in Gelatin Microsphere Matrix

To confirm that the hemostatic activity of recombinant human thrombin (rThrombin) is maintained when applied using the gelatin matrix and to evaluate performance characteristics of the matrix, non-GLP pharmacology studies were conducted using previously established bleeding models, rat heminephrectomy and rabbit liver injury. An additional model representing a type of bleeding common in vascular surgery procedures was also used to evaluate the rThrombin gelatin matrix. Key aspects of this model, which produced bleeding from a needle puncture in an arterial graft site, include a higher pressure and flow rate present at the bleeding site, and the use of anticoagulant in the animals. Together, these three bleeding models were used to confirm the performance and hemostatic activity of the rThrombin gelatin matrix under a range of conditions mimicking the intended clinical use.

Figure 7A:
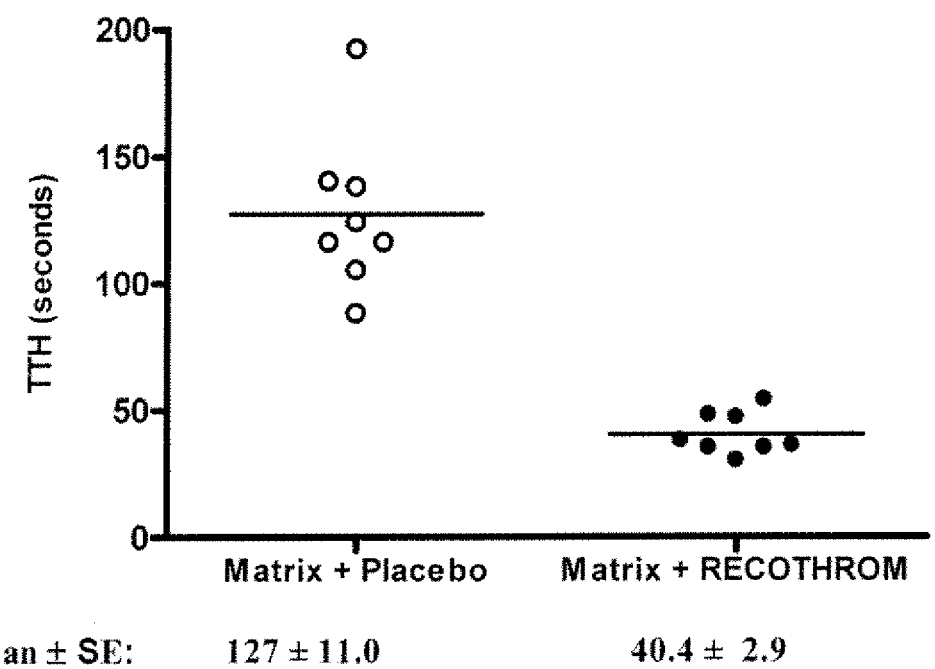
FIGS. 7A-7C are graphs showing time to topical hemostasis.

Example 14A: In Vivo Study: Rat Kidney Bleeding rThrombin and placebo, both applied with gelatin matrix, were compared in a blinded manner in the rat heminephrectomy model (n=8 per group). Briefly, this model involves creation of a standardized injury to the kidney, using a template to produce a sagittal cut and remove approximately 18% of the kidney mass. Test article (gelatin matrix suspended in solution containing rThrombin) or placebo (gelatin matrix suspended in solution containing the formulation for rThrombin without active ingredient) was applied to the cut surface via syringe, two gauze sponges were placed over the test article, and continuous digital pressure was applied for 30 sec. At the end of the 30 sec period, the gauze sponges were visually inspected for bleeding. In the event that time to hemostasis (TTH) was not achieved, gauze sponges were replaced and additional test article was applied. Digital pressure was alternated with visual inspection every 10-15 sec until TTH was achieved, up to a maximum time of 10 min. Time to hemostasis was noted when no visible blood was seen soaking through to the clean gauze sponges. Mean arterial blood pressure and body temperature were monitored throughout the experimental period. Time to hemostasis is shown in FIG. 7A or individual animals treated with rThrombin or placebo. A significant reduction in group mean TTH (p<0.0001, t-test) was observed in wounds treated with rThrombin applied using gelatin matrix as compared to placebo applied in the same manner. Hemostasis was eventually achieved with the placebo/gelatin treatment. The mean TTH was approximately 3-fold greater in this group than in the rThrombin/gelatin group, however. These data demonstrate the importance of rThrombin as the active hemostatic agent in this model.

Figure 7B:
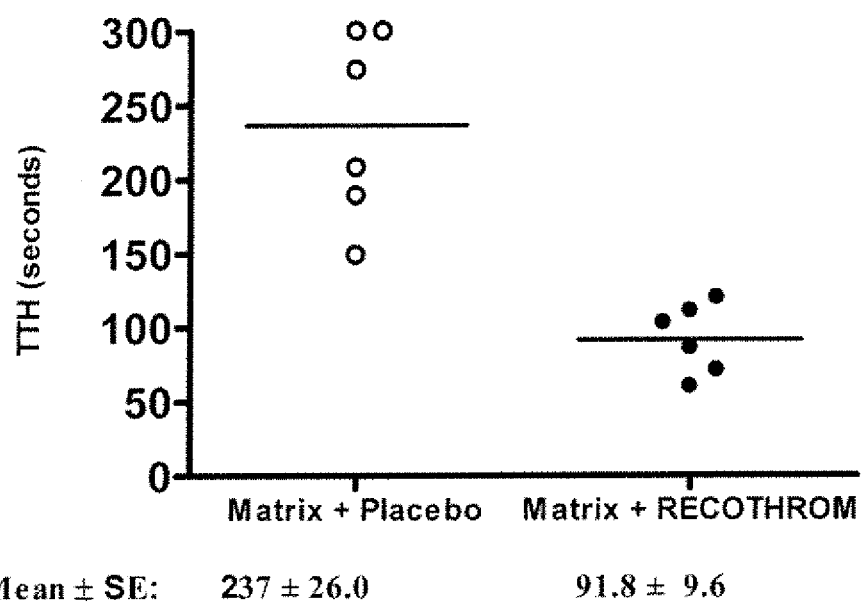

Example 14B: In Vivo Study: Rabbit Liver Bleeding rThrombin and placebo, both applied with gelatin matrix, were compared in a blinded manner in the rabbit liver injury model (n=6 per group). Briefly, this model involves creation of a standardized injury to the surface of the left medial liver lobe, using a template to remove a section of approximately 2 cm diameter. Test article (gelatin matrix suspended in solution containing rThrombin) or placebo (gelatin matrix suspended in solution containing the formulation for rThrombin without active ingredient) was applied to the cut surface via syringe, followed by placement of two gauze sponges over the test article and application continuous digital pressure for 60 sec. At the end of the 60-sec-period, the gauze sponges were visually inspected for bleeding. In the event that TTH was not achieved, gauze sponges were replaced and additional test article was applied. Digital pressure was alternated with visual inspection every 10-15 sec until TTH was achieved, up to a maximum time of 10 min. Time to hemostasis was noted when no visible blood was seen soaking through to the clean gauze sponges. Mean arterial blood pressure and body temperature were monitored throughout the experimental period. Time to hemostasis is shown in FIG. 7B for individual animals treated with rThrombin or placebo. A significant reduction in group mean TTH (p=0.0016, t-test) was observed in wounds treated with rThrombin applied using gelatin matrix as compared to placebo applied in the same manner. Although hemostasis was eventually achieved with the placebo/gelatin treatment, the mean TTH was more than two-fold greater in this group relative to that in the rThrombin/gelatin group. These data demonstrate the importance of rThrombin as the active hemostatic agent in this model.

Example 14C: In Vivo Study: Rabbit AV Shunt

A rabbit A-V shunt model was developed to mimic bleeding that could occur in a vascular surgery setting.

Briefly, this model involves producing an arterial-venous shunt linking the blood flow of the left carotid artery and the right jugular vein, using a PTFE graft segment about 2 cm in length to connect the catheters. Rabbits were treated with intravenous Heparin (100 U/kg i.v. bolus and 50 U/kg/hr) to maintain shunt patency. Mean arterial blood pressure (MAP), blood flow rate in the shunt, APTT, and body temperature were monitored throughout the experimental period. A baseline MAP of approximately 55 mm Hg was achieved prior to puncturing any of the grafts. Immediately following graft puncture with a suture needle, (reverse cutting needle size P-3), the test article or placebo was administered using a syringe for the gelatin matrix groups or a spray pump for liquid rThrombin groups. Grafts were immediately covered with gauze sponges and continuous digital pressure was applied for 60 sec. In the grafts treated with spray application placebo, the treatment was essentially equivalent to application of direct pressure alone. At the end of the 60 sec period, the gauze sponges were visually inspected for bleeding. In the event that TTH was not achieved, gauze sponges were replaced and additional test article was applied. Digital pressure was alternated with visual inspection every 10-15 sec until TTH was achieved. Time to hemostasis was noted when no visible blood was seen soaking through to the clean gauze sponges. In the event TTH was not achieved within the 5-minute study period, the study was terminated and 300 sec was recorded. At the conclusion of the study period, the catheters were clamped, flushed with saline, and a new PTFE segment was installed, provided the 55 mm Hg MAP criteria was met. Test articles were randomized among twenty-four grafts in four different animals for this study. A generalized estimating equations model was used to compare TTH measurements between treatment groups using SAS (Version 9.1.3).

Figure 7C:
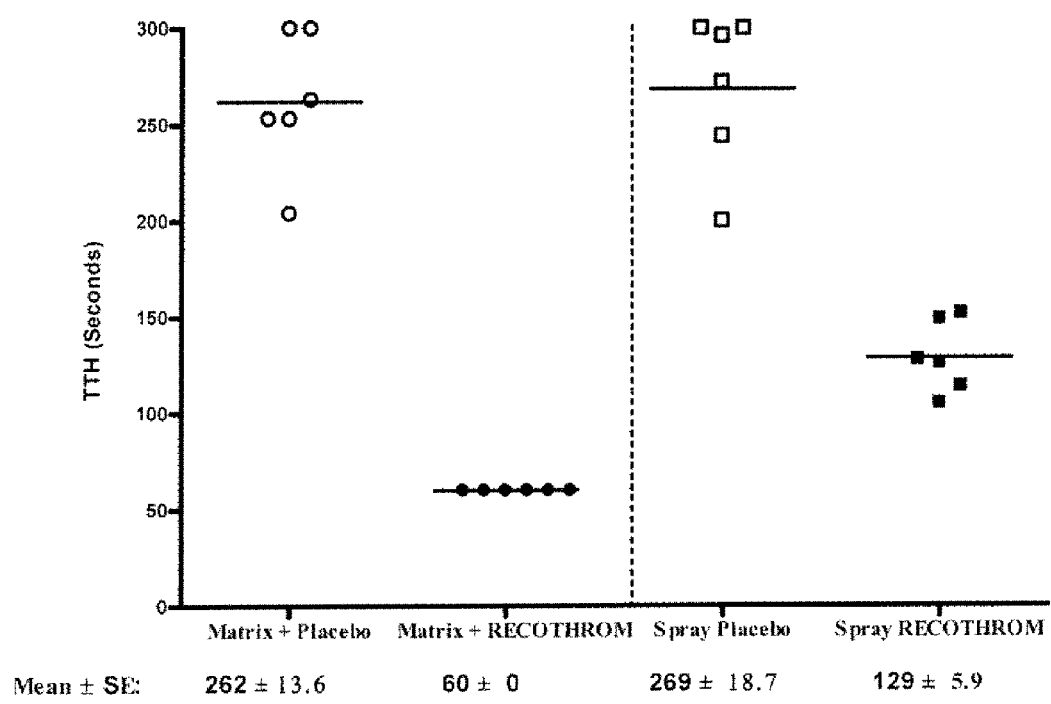

The primary purpose of the rabbit AV shunt model study was to confirm the hemostatic activity of rThrombin and evaluate performance of the gelatin matrix in a vascular bleeding application. rThrombin and placebo, both applied with gelatin matrix, were compared in a blinded manner in the rabbit A-V shunt model. Time to hemostasis (TTH) is shown in FIG. 7C for individual graft sites (n=6/group) treated with rThrombin or placebo applied using the gelatin matrix. A significant reduction in group mean TTH (p<0.0001) was observed in grafts treated with rThrombin as compared to placebo. All measurements of TTH for the rThrombin-treated grafts had the lowest possible value of 60 sec, compared to a much higher mean TTH in placebo-treated grafts including twp grafts in which hemostasis was not observed (300-sec maximal value).

A secondary purpose of this study was to assess the relative contributions of rThrombin and the gelatin matrix to hemostatic activity. Data from the rat heminephrectomy and rabbit liver injury model suggested that the matrix itself may possess some limited hemostatic activity independent of rThrombin. A passive hemostatic effect of the gelatin matrix is expected, based on its physical properties and ability to slow the flow of blood from a wound. Under conditions of the AV shunt model, however, the larger and more consistent difference between treatment groups clearly indicate that rThrombin provides the primary mode of action. This conclusion is further supported by comparing the effects of rThrombin delivered in the absence of gelatin matrix. This was accomplished by spray application of rThrombin, with blinded comparison to placebo. A significant reduction in group mean TTH was observed in grafts treated with rThrombin alone (FIG. 7C) as compared to the gelatin matrix/placebo group (p<0.0001), or to the group treated with placebo alone (p<0.0001).

Example 15. Comparison of Microsphere Size in rThrombin-Assisted TTH

Gelatin microspheres may be sieved to obtain microparticles of a particular size range. In the case of CultiSpher®-S macroporous gelatin microcarrier microspheres, the material can be sieved to include sizes of about 130 µm to 380 µm diameter. During production of a batch, approximately half of the material may be lost as the fraction of microspheres of about <130 µm diameter. A comparison of flowable thrombin devices including all gelatin microsphere material with a size of <380 µm diameter with a flowable device including gelatin microsphere material with a size of about 130-380 µm diameter was undertaken.

Figure 8:
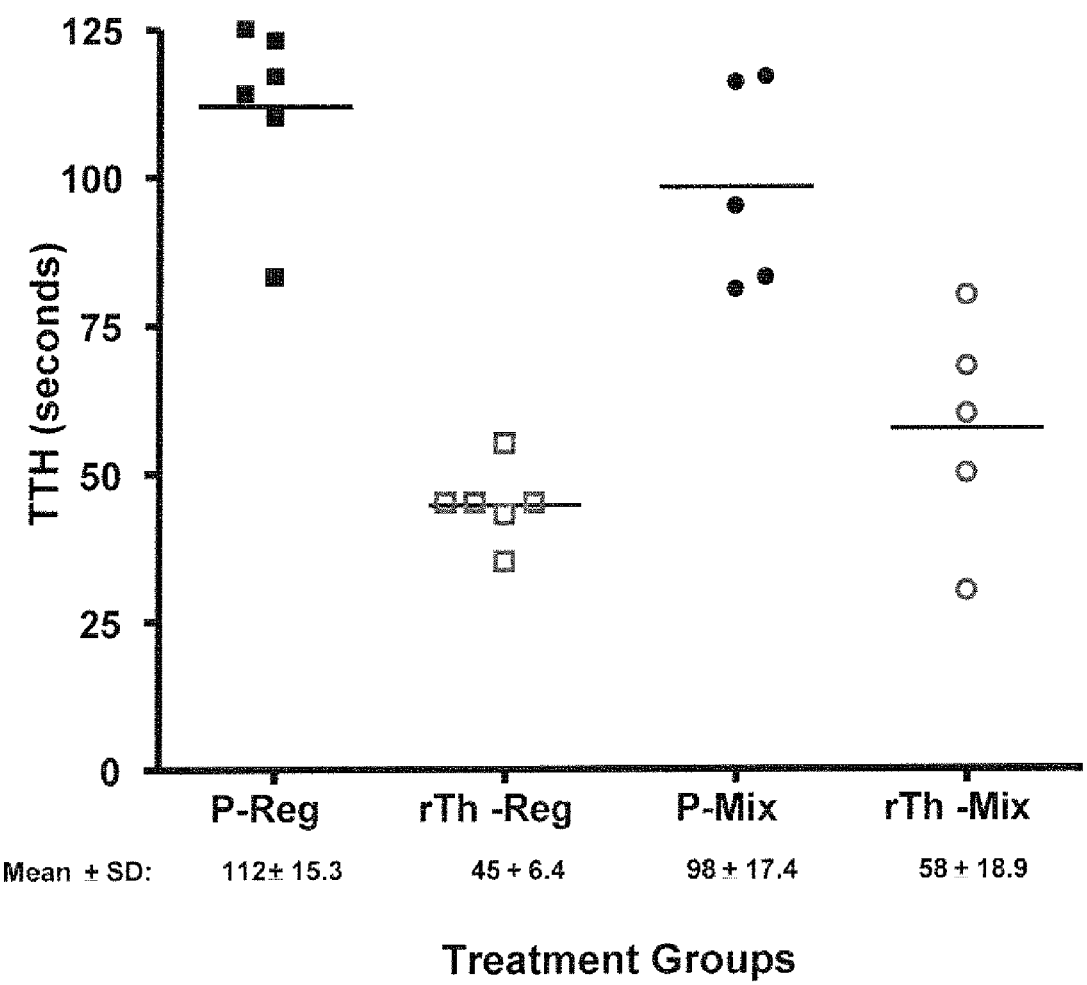
FIG. 8 shows the TTH in a rat heminephrectomey model, comparing a composition of thrombin and 130-380 μm polymer microspheres with a composition of 1000 IU/mL thrombin and a 50:50 weight ratio mixture of <130 μm:130-380 μm polymer microspheres. P=mixed with placebo, rTh=mixed with 1000 IU/mL thrombin.

More specifically, rThromin in CultiSpher®-S macroporous gelatin microcarrier N18051, size about 130-380 µm diameter, was compared with rThrombin in CultiSpher®-S macroporous gelatin microcarrier 19122, size about <130 µm diameter mixed at a 50:50 weight ratio with microcarriers of 130-380 µm diameter. When tested in the rat heminephrectomey model, a higher and more variable TTH was observed in the mixed batch having 50%<130 µm diameter than in the batch having standard 130-380 µm diameter formulation (FIG. 8). Additionally, greater adherence to gauze and re-bleeding was observed in the mixed batch of 50%<130 µm diameter than the standard batch of 130-380 µm diameter formulation. Including smaller microparticles lead to reduction in efficacy in this model, and beads with the size range of about 130 µm to about 380 µm in diameter proved more effective.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:
1. A kit including a hemostatic composition comprising:
a plurality of porous cross-linked gelatin microspheres;
a wetting agent;
a suspending agent; and
thrombin
wherein the wetting agent and the suspending agent are present in a ratio of microspheres:the wetting agent and the suspending agent of 3:1 to 60:1 (w/w), wherein the wetting agent is poloxamer 188 and the suspending agent is carboxymethylcellulose, wherein the porous cross-linked gelatin microspheres have a diameter from about 50 µm to about 500 µm, inclusive, when fully hydrated, and wherein the porous cross-linked gelatin microspheres have a pore diameter from about 15 µm to about 25 µm, inclusive.
2. The kit of claim 1, further comprising a hemostatic composition delivery device comprising at least one syringe.
3. The kit of claim 2, wherein the syringe contains the hemostatic composition.
4. The kit of claim 1, further comprising a diluent.
5. The kit of claim 3, wherein the delivery device further comprises a second syringe and a diluent, wherein said diluent, optionally, contains or is plasma.
6. The kit of claim 5, wherein the thrombin is present in the diluent.

7. The kit of claim 5, wherein the second syringe and the syringe containing the hemostatic composition are interconnected.

8. The kit of claim 7, wherein the syringes are interconnected by a male/female luer lock system.

9. The kit of claim 1, wherein the hemostatic composition is a dry powder.

10. The kit of claim 1, wherein the thrombin concentration is in a range of about 1,000 IU to about 2,000 IU per mL of rehydrated microsphere gel, inclusive.

11. The kit of claim 1, wherein the thrombin concentration is in a range of about 1,000 IU to about 5,000 IU per mL of rehydrated microsphere gel, inclusive.

12. The kit of claim 1, wherein the thrombin concentration is in a range of about 5,000 IU to about 50,000 IU per mL of rehydrated microsphere gel, inclusive.

13. The kit of claim 1, wherein the hemostatic composition has been compressed into a pledget and dried.

* * * * *